(12) United States Patent
Takehara et al.

(10) Patent No.: US 10,703,719 B2
(45) Date of Patent: Jul. 7, 2020

(54) METHOD FOR PRODUCING 5-HYDROXYPIPERIDINE-2-CARBOXYLIC ACID

(71) Applicant: API CORPORATION, Tokyo (JP)

(72) Inventors: Jun Takehara, Fukuoka (JP); Masato Murai, Fukuoka (JP); Takashi Ohtani, Kanagawa (JP); Tomoko Maeda, Kanagawa (JP); Tsugihiko Hidaka, Fukuoka (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 15/965,289

(22) Filed: Apr. 27, 2018

(65) Prior Publication Data

US 2018/0244619 A1 Aug. 30, 2018

Related U.S. Application Data

(62) Division of application No. 15/705,349, filed on Sep. 15, 2017, now Pat. No. 9,988,351, which is a division of application No. 15/108,141, filed as application No. PCT/JP2014/084518 on Dec. 26, 2014, now Pat. No. 9,790,181.

(30) Foreign Application Priority Data

Dec. 27, 2013 (JP) ................................ 2013-272766

(51) Int. Cl.
*C07D 211/60* (2006.01)
*C07C 309/66* (2006.01)
*C07C 233/47* (2006.01)
*C07D 498/08* (2006.01)

(52) U.S. Cl.
CPC .......... *C07D 211/60* (2013.01); *C07C 233/47* (2013.01); *C07C 309/66* (2013.01); *C07D 498/08* (2013.01); *Y02P 20/55* (2015.11)

(58) Field of Classification Search
CPC ... C07D 498/08; C07D 211/60; C07C 309/66; C07C 233/47
USPC ........................................................ 544/105
See application file for complete search history.

(56) References Cited

U.S. PATENT DOCUMENTS 5,164,372 A 11/1992 Matsuo
6,399,600 B1 6/2002 Wolfe et al.
2007/0155983 A1 7/2007 Ikemoto
(Continued)

FOREIGN PATENT DOCUMENTS

CN 102477019 A * 5/2012
WO 2005/014508 2/2005
WO 2006/125974 11/2006
(Continued)

OTHER PUBLICATIONS

Jiang et al. Tetrahedron: Asymmetry (2001), 12(20), 2835-2843. (Year: 2001).*
(Continued)

*Primary Examiner* — Kahsay Habte
(74) *Attorney, Agent, or Firm* — Greenblum & Bernstein, P.L.C.

(57) ABSTRACT

A method for producing (2S,5S)/(2R,5R)-5-hydroxypiperidine-2-carboxylic acid represented by the formula (10) below:

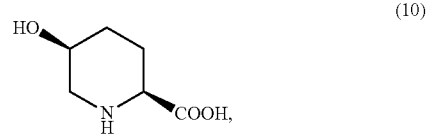

the method including removing the protecting group from the hydroxyl group in a compound represented by formula (7) below:

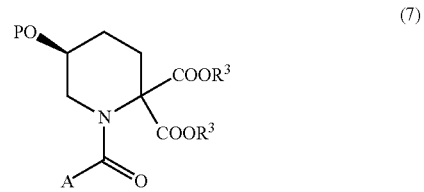

(wherein P represents a protecting group, R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms) to synthesize a compound represented by formula (8) below:

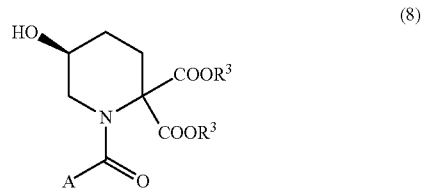

(wherein R³ represents an alkyl group containing 1 to 4 carbon atoms, and A represents an alkyl group containing 1
(Continued)

to 10 carbon atoms, an aryl group containing 6 to 12 carbon atoms, an alkyloxy group containing 1 to 4 carbon atoms, or an aralkyloxy group containing 7 to 20 carbon atoms).

13 Claims, 1 Drawing Sheet

(56) References Cited

U.S. PATENT DOCUMENTS

| | | |
|---|---|---|
| 2015/0118719 A1 | 4/2015 | Chen |
| 2015/0239906 A1 | 8/2015 | Maeda et al. |

FOREIGN PATENT DOCUMENTS

| | | |
|---|---|---|
| WO | 2009/011551 | 1/2009 |
| WO | 2010/126820 | 11/2010 |
| WO | 2013/169725 | 11/2013 |
| WO | 2014/098188 | 6/2014 |

OTHER PUBLICATIONS

Japanese Office Action issued with respect to Japanese Application No. 2015-555046, dated Feb. 5, 2019, with English translation.
Beyerman et al., "Stereospecific Synthesis and Optical Resolution of 5-hydroxypipecolic Acid", Recueil, 1959, vol. 78, pp. 648-658.
European Search Report issued with respect to Application No. 18212248.1, dated Feb. 19, 2019.
Adams et al., "An efficient route to the a-methyl ester of L-glutamic acid, and its conversion into cis-5-hydroxy-L-pipecolic acid", Chem. Commun., 1996, pp. 349-350.
Bailey et al., "Chiral Synthesis of 5-Hydroxy-(L)-Pipecolic Acids from (L)-Glutamic Acid", Tetrahedron Letters, 1988, vol. 29, No. 18, 2231-2234.
Letavic et al., "Synthesis and Biological Activity of Selective Pipecolic Acid-Based TNF-α Converting Enzyme (TACE) Inhibitors", Bioorg. Med. Chem. Lett. , 2002, vol. 12, 1387-1390.
Jung et al., "Diastereoselective synthesis of (2S,5S)- and (2S, 5R)-N-benzyloxycarbonyl-5-hydroxypipecolic acids from trans-4-hydroxy-L-proline", Tetrahedron: Asymmetry, 2006, pp. 2479-2486, vol. 17, No. 17.
Hoarau et al., "Synthesis of Enantiomerically Pure (2R, 5S)- and (2R, 5R)-5-Hydroxypipecolic Acid from Glycinate Schiff Bases", Tetrahedron: Asymmetry, 1996, pp. 2585-2593, vol. 7, No. 9.
Herdeis et al., "An Efficient Synthetic Method for the Preparation of (±)-Baikiain and its Derivatives", Arch. Pharm., 1993, pp. 297-301, vol. 326, No. 5.
Kobayashi et al., "Synthesis of macrosphelides H and G", Tetrahedron Letters, 2002, pp. 4381-4384, vol. 43.
Jiang et al., "Stereoselective Synthesis of Kurzilactone and determination of its absolute configuration", Tetrahedron: Asymmetry, vol. 12, 2001, pp. 2835-2843.
International Search Report issued with respect to application No. PCT/JP2014/084518, dated Mar. 31, 2015.
Notification of transmittal of translation of the International Preliminary Report on Patentability issued with respect to application No. PCT/JP2014/084518, dated Jul. 7, 2016.
Letavic et al., Bioorganic & Medicinal Chemistry Letters (2002), 12 (10), pp. 1387-1390.
Hagiwara et al., Journal of Medical Chemistry (1994), 37 (13), pp. 2090-2099.
European Search Report issued with respect to Application No. 14873766.1, dated Jul. 10, 2017.
Claus Herdeis et al., "Synthesis of (2S, 4S, 5S)-5-hydroxy-4-methylpipecolic acid via amide methylenation of 5-hydroxy-4-methyl-2-piperidinone with dimethyltitanocene", Tetrahedron: Asymmetry, vol. 8, No. 7, 1997, pp. 1115-1121.
Hearing notice of references, India patent office, Application No. 201617025320, dated Jul. 16, 2019, 3 pages.

* cited by examiner

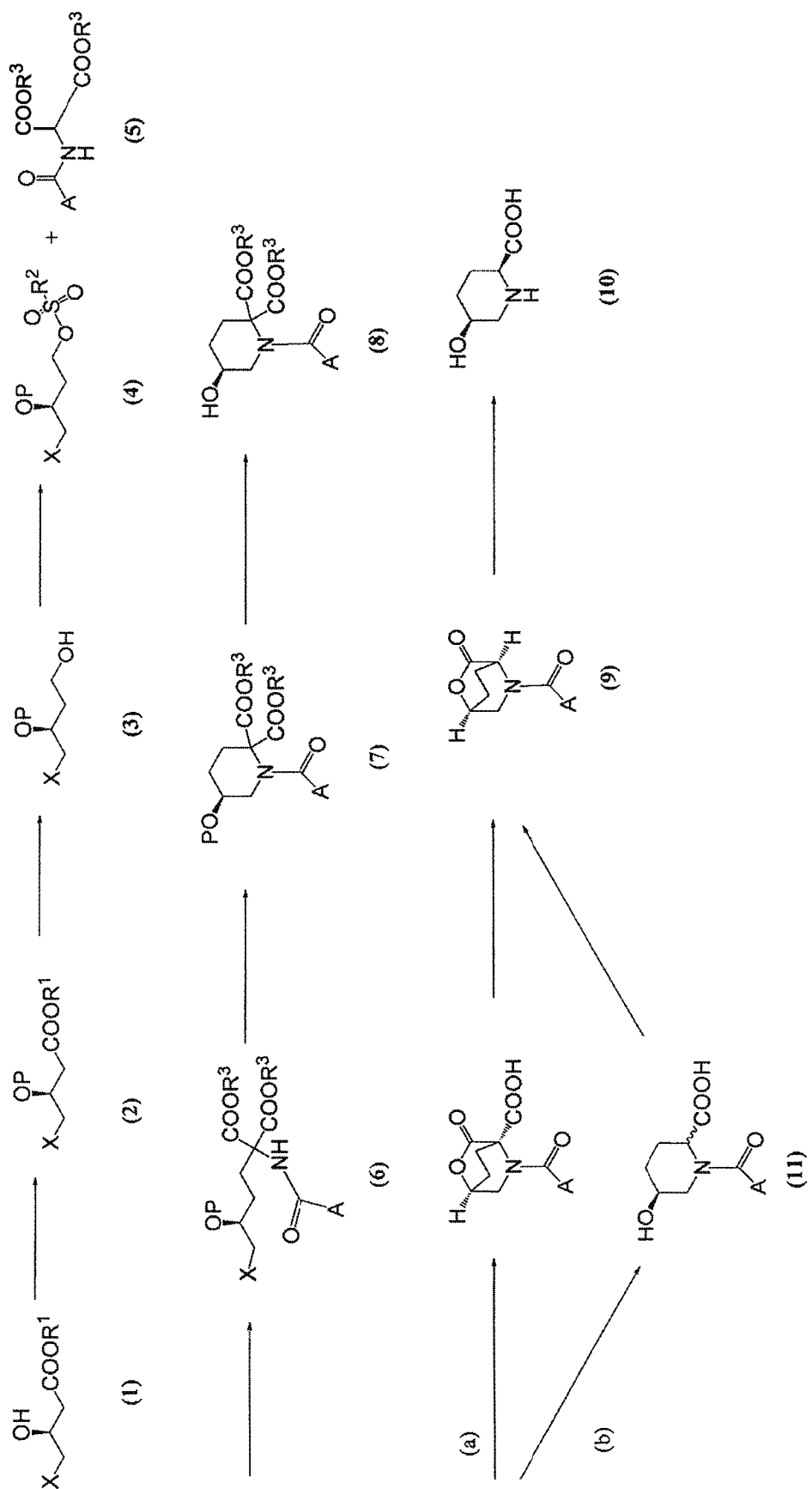

METHOD FOR PRODUCING 5-HYDROXYPIPERIDINE-2-CARBOXYLIC ACID

The present application is a Divisional application of U.S. application Ser. No. 15/705,349, filed Sep. 15, 2017, which is Divisional application of U.S. application Ser. No. 15/108,141, filed Jun. 24, 2016, which is a National Stage of International Patent Application No. PCT/JP2014/084518 filed Dec. 26, 2014, which claims priority to Japanese Application No. 2013-272766 filed Dec. 27, 2013. The disclosures of U.S. application Ser. No. 15/705,349, Ser. No. 15/108,141 and International Patent Application No. PCT/JP2014/084518 are incorporated by reference herein in their entireties.

TECHNICAL FIELD

The present invention relates to a method for producing (2S,5S)/(2R,5R)-5-hydroxypiperidine-2-carboxylic acid and synthetic intermediates thereof. (2S,5S)/(2R,5R)-5-hydroxypiperidine-2-carboxylic acid, which is produced by the method of the present invention, is useful as a synthetic intermediate for a β-lactamase inhibitor and the like.

BACKGROUND ART (2S,5S)/(2R,5R)-5-hydroxypiperidine-2-carboxylic acid is a useful intermediate for the synthesis of an agent and the like that inhibits β-lactamases in bacteria exhibiting the resistance against the β-lactam class of antibiotics, which β-lactamases are the major cause of the resistance in the bacteria.

A production method using glutamic acid or pyroglutamic acid as a starting raw material has been known as a method for producing (2S,5S)/(2R,5R)-5-hydroxypiperidine-2-carboxylic acid. Specifically, Patent Document 1 describes that a protected 5-hydroxypiperidine-2-carboxylic acid compound as an intermediate of N-protected oxo-azacycloalkylcarboxylic acids is produced from pyroglutamic acid as a starting raw material through the homologation process to increase carbon atoms and the cyclization process.

Moreover, Non-Patent Document 1 describes that a protected 5-hydroxypiperidine-2-carboxylic acid compound is produced from glutamine as a starting raw material through the homologation process to increase carbon atoms and the cyclization process.

Non-Patent Document 2 describes that a mixture of stereoisomers of a protected 5-hydroxypiperidine-2-carboxylic acid compound is produced from a protected glutamic acid compound as a starting raw material through the homologation process to increase carbon atoms and the cyclization process.

Non-Patent Document 3 describes that a protected 5-hydroxypiperidine-2-carboxylic acid compound is produced from a protected pyroglutamic acid compound as a starting raw material through the homologation process to increase carbon atoms and the cyclization process.

Patent Document 2 describes that a protected 5-hydroxypiperidine-2-carboxylic acid compound is produced from a protected pyroglutamic acid compound as a starting raw material through the homologation process to increase carbon atoms and the cyclization process in one step.

PRIOR ART DOCUMENTS

Patent Documents

Patent Document 1: WO2010/126820
Patent Document 2: WO2006/125974

Non-Patent Documents

Non-Patent Document 1: P. D. Bailey et al., Chem. Commun. 1996, 349.
Non-Patent Document 2: P. D. Bailey et al., Tetrahedron Lett. 1988, 29, 2231.
Non-Patent Document 3: M. A. Letavic et al., Bioorg. Med. Chem. Lett. 2002, 12, 1387.

SUMMARY OF THE INVENTION

Technical Problem

The method described in Patent Document 1 to produce (2S,5S)/(2R,5R)-5-hydroxypiperidine-2-carboxylic acid requires a very expensive iridium catalyst to be used and therefore is not suitable for the industrial production.

The production method described in Non-Patent Document 1 is difficult to be employed in the industrial production because the method also requires an expensive rhodium catalyst to be used and, furthermore, comprises the step of using diazomethane, which is difficult to use in industrial applications.

The production method described in Non-Patent Document 2 is likewise difficult to be employed in the industrial production because the method also comprises the step of using diazomethane, which is difficult to use in industrial applications, and further comprises a problem regarding an obtainable compound, in which the compound is obtained as a mixture of stereoisomers.

The production methods described in Non-Patent Document 3 and Patent Document 2 are likewise difficult to be employed in the industrial production because the methods comprise the step of using TMS diazomethane, which is expensive and difficult to use in industrial applications. Furthermore, the production method described in Patent Document 2 requires an expensive rhodium catalyst to be used. Either of the production methods described in Non-Patent Document 3 and Patent Document 2 requires the reaction to be performed at a quite low temperature and therefore is difficult to be employed in the industrial production.

In view of the above-mentioned problems, an object of the present invention is to provide a method for producing (2S,5S)/(2R,5R)-5-hydroxypiperidine-2-carboxylic acid and synthetic intermediates thereof including achiral and chiral molecules, the method available for practical use in the industrial production.

Solution to Problem

The inventors have intensively studied to solve the above-described problems and consequently found that optically active substances of (2S,5S)/(2R,5R)-5-hydroxypiperidine-2-carboxylic acids can be efficiently synthesized by using particular synthetic intermediates, and thereby completed the present invention.

That is, the present invention is as follows.

<1> A method for producing (2S,5S)/(2R,5R)-5-hydroxypiperidine-2-carboxylic acid represented by the formula (10) below:

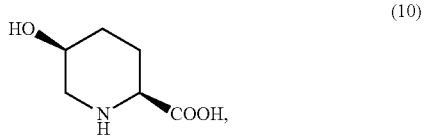

the method comprising (i) the step 4 of:

removing the protecting group from the hydroxyl group in a compound represented by the formula (7) below:

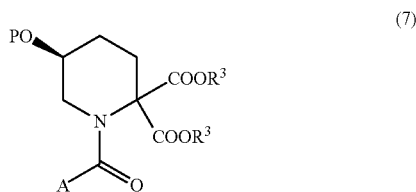

(wherein P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms) to synthesize a compound represented by the formula (8) below:

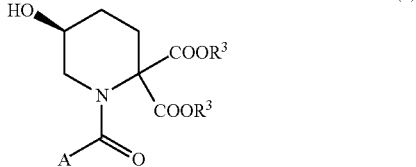

(wherein $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<2> The method for producing (2S,5S)/(2R,5R)-5-hydroxypiperidine-2-carboxylic acid according to <1>, the method further comprising (ii) the step 5 of:

(a) in the compound (8), hydrolyzing the ester groups, allowing one of the carboxyl groups to react with the hydroxyl group to allow the lactonization, and further decarboxylating the other carboxyl group; or (b) in the compound (8), hydrolyzing the ester groups, decarboxylating one of the carboxyl groups to form a stereoisomeric mixture of a 2-monocarboxylic acid, and then isomerizing and lactonizing the stereoisomeric mixture; to synthesize a compound represented by the formula (9) below:

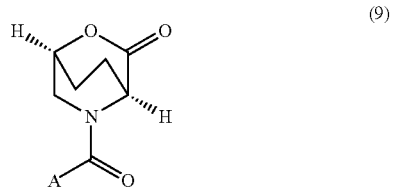

(wherein A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<3> The method for producing (2S,5S)/(2R,5R)-5-hydroxypiperidine-2-carboxylic acid according to <1> or <2>, further comprising (iii) the step 6 of:

cleaving the amide bond in the compound (9) and hydrolyzing the lactone in the compound (9) to synthesize (2S,5S)/(2R,5R)-5-hydroxypiperidine-2-carboxylic acid.

<4> The method for producing (2S,5S)/(2R,5R)-5-hydroxypiperidine-2-carboxylic acid according to <2> or <3>, wherein the step of decarboxylating the carboxyl group in the step 5(a) or the step 5(b) is performed in the presence of an organic base.

<5> A method for producing the compound represented by the formula (7) below:

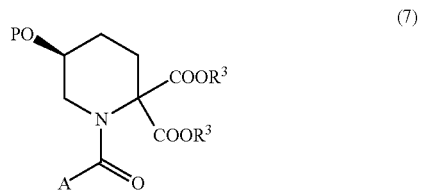

(wherein P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms), the method comprising the step 1 of:

protecting the hydroxyl group with a protecting group in a compound represented by the formula (1) below:

(wherein X represents Cl, Br, or I, and $R^1$ represents a hydrogen atom or an optionally substituted alkyl group containing 1 to 4 carbon atoms) to synthesize a compound represented by the formula (2) below:

(wherein X represents Cl, Br, or I, $R^1$ represents a hydrogen atom or an optionally substituted alkyl group containing 1 to 4 carbon atoms, and P represents a protecting group)

and then reducing the ester group in the compound (2) to synthesize a compound represented by the formula (3) below:

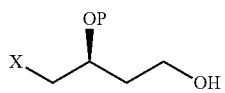
(3)

(wherein X represents Cl, Br, or I, and P represents a protecting group).

<6> The method for producing the compound (7) according to <5>, wherein the method comprises (i) the step 2 of:
esterifying the hydroxyl group in the compound (3) to a sulfonate group to synthesize a compound represented by the formula (4) below:

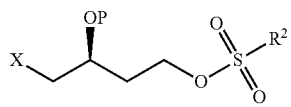
(4)

(wherein X represents Cl, Br, or I, $R^2$ represents an aryl group containing 6 to 12 carbon atoms, an alkyl group containing 1 to 10 carbon atoms, or an aralkyl group containing 7 to 20 carbon atoms)
and allowing the compound (4) to react with a compound represented by the formula (5) below:

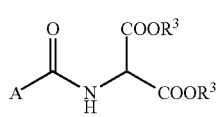
(5)

(wherein $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms)
to synthesize a compound represented by the formula (6) below:

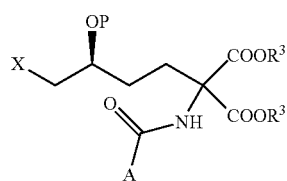
(6)

(wherein X represents Cl, Br, or I, P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms); and
(ii) the step 3 of:
cyclizing the compound (6) to synthesize the compound represented by the formula (7) below:

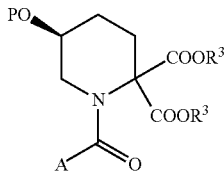
(7)

(wherein P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<7> The method for producing the compound (7) according to <6>, wherein the reaction of the compound (4) with the compound (5) in the step 2 is performed in the presence of an iodide salt.

<8> The method for producing the compound (7) according to <6> or <7>, wherein the cyclizing reaction of the compound (6) in the step 3 is performed in the presence of a quaternary ammonium salt.

<9> The method for producing (2S,5S)/(2R,5R)-5-hydroxypiperidine-2-carboxylic acid according to any one of <1> to <4>, wherein the compound (7) is synthesized by the method according to any one of <5> to <8>.

<10> A method for producing the compound represented by the formula (8), the method comprising (i) the step 4 of:
removing the protecting group from the hydroxyl group in the compound represented by the formula (7) below:

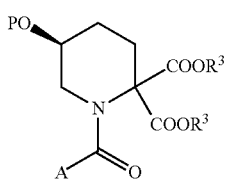
(7)

(wherein P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms) to synthesize the compound represented by the formula (8) below:

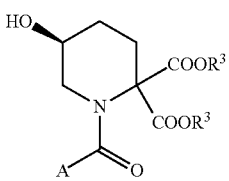
(8)

(wherein $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<11> A method for producing the compound represented by the formula (9), the method comprising (i) the step 4 of:

removing the protecting group from the hydroxyl group in the compound represented by the formula (7) below:

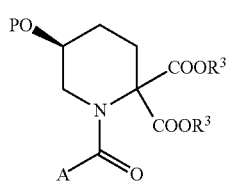

(7)

(wherein P represents a protecting group, R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms) to synthesize the compound represented by the formula (8) below:

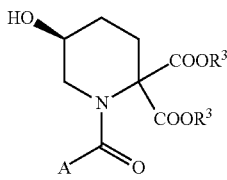

(8)

(wherein R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms)

and (ii) the step 5 of:

(a) in the compound (8), hydrolyzing the ester groups, allowing one of the carboxyl groups to react with the hydroxyl group to allow the lactonization, and further decarboxylating the other carboxyl group; or (b) in the compound (8), hydrolyzing the ester groups, decarboxylating one of the carboxyl groups to form a stereoisomeric mixture of a 2-monocarboxylic acid, and then isomerizing and lactonizing the stereoisomeric mixture; to synthesize the compound represented by the formula (9) below:

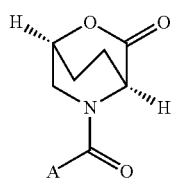

(9)

(wherein A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<12> A compound represented by the formula (9a) below:

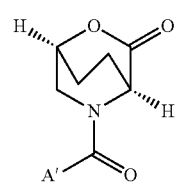

(9a)

(wherein A' represents an aryl group containing 6 to 12 carbon atoms or an alkyl group containing 1 to 10 carbon atoms).

<13> A compound or a salt thereof, the compound represented by the formula (11a) below:

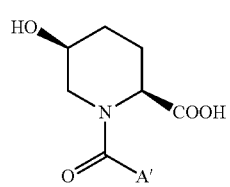

(11a)

(wherein A' represents an aryl group containing 6 to 12 carbon atoms or an alkyl group containing 1 to 10 carbon atoms)

or the formula (11 b) below:

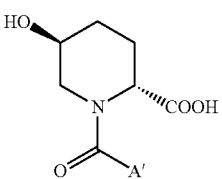

(11b)

(wherein A' represents an aryl group containing 6 to 12 carbon atoms or an alkyl group containing 1 to 10 carbon atoms).

<14> A compound represented by the formula (8) below or a dicarboxylic acid salt thereof:

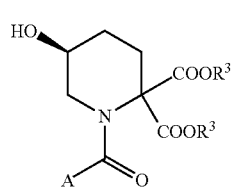

(8)

(wherein R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<15> A compound represented by the formula (7) below:

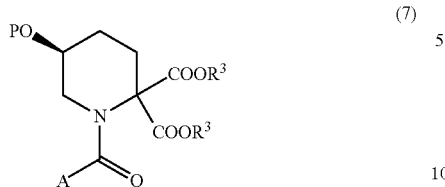
(7)

(wherein P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<16> A compound represented by the formula (6a) below:

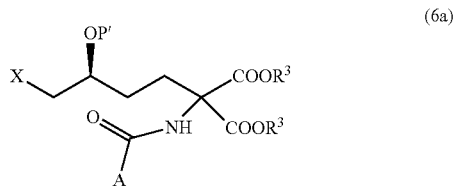
(6a)

(wherein X represents Cl, Br, or I, P' represents a tetrahydropyranyl group, methoxymethyl group, ethoxyethyl group, tert-butyl group, or tert-butyldimethylsilyl group, and $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

<17> A compound represented by the formula (4a) below:

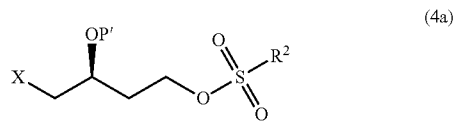
(4a)

(wherein X represents Cl, Br, or I, P' represents a tetrahydropyranyl group, methoxymethyl group, ethoxyethyl group, tert-butyl group, or tert-butyldimethylsilyl group, and $R^2$ represents an aryl group containing 6 to 12 carbon atoms, an alkyl group containing 1 to 10 carbon atoms, or an aralkyl group containing 7 to 20 carbon atoms).

<18> A compound represented by the formula (3a) below:

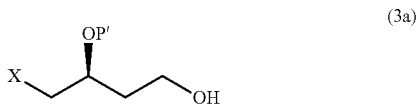
(3a)

(wherein X represents Cl, Br, or I, and P' represents a tetrahydropyranyl group, methoxymethyl group, ethoxyethyl group, tert-butyl group, or tert-butyldimethylsilyl group).

<19> A compound represented by the formula (2a) below:

(2a)

(wherein X represents Cl, Br, or I, $R^1$ represents a hydrogen atom or an optionally substituted alkyl group containing 1 to 4 carbon atoms, P" represents a tetrahydropyranyl group or ethoxyethyl group).

Advantageous Effect of the Invention

The present invention can provide (2S,5S)/(2R,5R)-5-hydroxypiperidine-2-carboxylic acid and a production method therefor excellent in safety and operability and available for practical use in the industrial production. Moreover, the present invention can provide novel synthetic intermediates for the production of (2S,5S)/(2R,5R)-5-hydroxypiperidine-2-carboxylic acid. (2S,5S)/(2R,5R)-5-hydroxypiperidine-2-carboxylic acid, which is produced by the production method of the present invention, is available as a starting material in the production of a β-lactamase inhibitor and the like.

BRIEF DESCRIPTION OF THE DRAWINGS

FIG. 1 shows one aspect of the scheme for the synthesis of (2S,5S)/(2R,5R)-5-hydroxypiperidine-2-carboxylic acid. In the drawing, X represents Cl, Br, or I. P represents a protecting group. A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms. $R^1$ represents a hydrogen atom or an optionally substituted alkyl group containing 1 to 4 carbon atoms. $R^2$ represents an aryl group containing 6 to 12 carbon atoms, an alkyl group containing 1 to 10 carbon atoms, or an aralkyl group containing 7 to 20 carbon atoms. $R^3$ represents an alkyl group containing 1 to 4 carbon atoms.

DESCRIPTION OF THE EMBODIMENTS

Now, the present invention will be described in detail.
In the present specification, the "compound represented by the formula (1)" may be referred to as the "compound (1)" and this is true of any compounds represented by the other formulae.
In the present specification, Cl refers to a chlorine atom, Br refers to a bromine atom, I refers to an iodine atom, and Et refers to an ethyl group.
[1] Production Method
The present invention is characterized in that optically active substances of (2S,5S)/(2R,5R)-5-hydroxypiperidine-2-carboxylic acids are produced by using a particular synthetic intermediate represented by the formula (8) below:

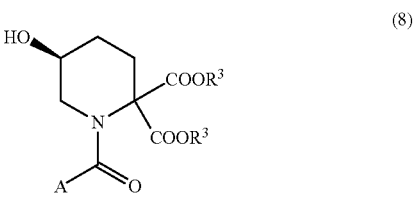
(8)

(wherein R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms) or the formula (9) below:

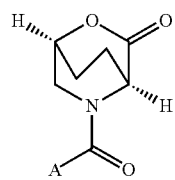

(9)

(wherein A represents an alkyl group containing 1 to 10 carbon atoms, an aryl group containing 6 to 12 carbon atoms, or an alkyloxy group containing 1 to 4 carbon atoms, an aralkyloxy group containing 7 to 20 carbon atoms).

The compound (8) can be synthesized by ordinary procedures of organic chemistry and is preferably synthesized by the step 4 below.

The step 4 is a method to produce the compound represented by the formula (8) (the compound (8)) from a compound (7) as a raw material.

In the step 4, the protecting group can be removed from the hydroxyl group in the compound represented by the formula (7) below:

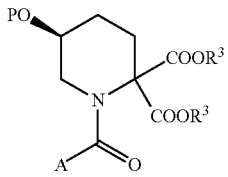

(7)

(wherein P represents a protecting group, R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms) to synthesize the compound represented by the formula (8) below:

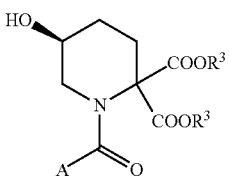

(8)

(wherein R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

Conditions commonly used in deprotection of each protection group can be employed as conditions for the deprotection. Typically, an acid or a combination of an acid catalyst and an alcohol is used.

As the acid used for the deprotection, an inorganic acid such as hydrochloric acid, sulfuric acid, phosphoric acid and the like, or an organic acid such as methanesulfonic acid, p-toluenesulfonic acid, oxalic acid, trifluoroacetic acid, formic acid, acetic acid and the like is typically used and hydrochloric acid or p-toluenesulfonic acid is preferably used.

As the acid catalyst, an inorganic acid such as hydrochloric acid, sulfuric acid and the like, or an organic acid such as methanesulfonic acid, p-toluenesulfonic acid and the like is typically used and hydrochloric acid or p-toluenesulfonic acid is preferably used.

As the alcohol, methanol, ethanol, n-propanol, 2-propanol, n-butanol or the like is typically used and methanol is preferably used.

For example, in cases where P in the formula (7) is tetrahydropyranyl group or ethoxyethyl group, hydrochloric acid is preferably applied as a catalyst in methanol solvent and the deprotection can easily be achieved in this method.

Out of compounds represented by the formula (8), a compound represented by the formula (8a) below:

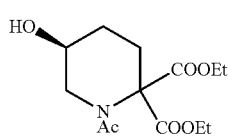

(8a)

(wherein Ac represents an acetyl group)
is crystalline and therefore is easily isolated and purified by crystallization after the deprotection so that the compound (8a) of high purity can be synthesized. Because (2S,5S)/(2R,5R)-5-hydroxypiperidine-2-carboxylic acid of high purity can be synthesized by performing the synthesis using the compound (8a) of high purity, the compound (8a) is particularly preferable as the synthetic intermediate. As the crystallization solvent, for example, toluene or a mixed solvent of toluene and heptane can be used.

Incidentally, R³ and A in the compound (8) are synonymous with R³ and A in the compound (5) described below.

The compound (9) can be synthesized by ordinary procedures of organic chemistry and is preferably synthesized by the step 5 below.

The step 5 is a method to produce the compound represented by the formula (9) (the compound (9)) from the compound (8) as a raw material. The following step 5(a) or 5(b) is preferable as the step 5.

In the step 5(a), in the compound (8), the ester groups are hydrolyzed, one of the carboxyl groups is allowed to react with the hydroxyl group to allow the lactonization, and the other carboxyl group is further decarboxylated to synthesize the compound represented by the formula (9) below:

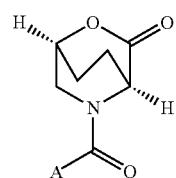

(9)

(wherein A represents an alkyl group containing 1 to 10 carbon atoms, an aryl group containing 6 to 12 carbon atoms, an alkyl group containing 1 to 10 carbon atoms, an aryl group containing 6 to 12 carbon atoms, or an alkyloxy group containing 1 to 4 carbon atoms, an aralkyloxy group containing 7 to 20 carbon atoms).

In the step 5(a), the ester groups in the compound (8) are first hydrolyzed. A base is used in the hydrolysis of the ester groups.

Water, methanol, ethanol or the like is used as a reaction solvent.

As the base, sodium hydroxide, potassium hydroxide or the like can be used and sodium hydroxide is preferable among others.

The amount of the base to be used is typically 2- to 10-fold, preferably 2- to 5-fold, relative to the amount of the compound (8) on the molar basis.

The reaction temperature is not particularly limited but is typically 0° C. to 50° C. and preferably 0° C. to 10° C.

The reaction time is not particularly limited but is typically for 1 to 24 hours and preferably for 5 to 10 hours.

Next, one of the carboxyl groups is allowed to react with the hydroxyl group to allow the lactonization after the ester groups in the compound (8) are hydrolyzed (ester degradation).

To perform the decarboxylation reaction after the lactonization, the dicarboxylic acid obtained by the ester degradation is first allowed to react with a dehydrating agent to induce the carboxyl group in the cis position with respect to the hydroxyl group at position 5 to be lactonized.

As the dehydrating agent, a commonly used dehydrating agent such as, for example, acetic anhydride, acetyl chloride, or thionyl chloride can be used.

The reaction solvent is not particularly limited as long as it does not inhibit the reaction, but acetic acid or a mixed solvent of acetic acid and toluene is preferably used.

The amount of the dehydrating agent to be used is typically 1- to 20-fold, preferably 1- to 5-fold, relative to the amount of the compound (8), in which the ester groups have been hydrolyzed, on the molar basis.

The reaction temperature is not particularly limited but is typically 0° C. to 80° C. and preferably 30° C. to 60° C.

The reaction time is not particularly limited but is typically 1 to 12 hours and preferably 2 to 5 hours.

After one of the carboxyl groups is lactonized, the other carboxyl group is further decarboxylated.

When the other remaining carboxyl group is further decarboxylated, protonation occurs after the decarboxylation in a stereoselective manner due to the steric structure fixed by the lactonization and thus the compound (9) in the 5-acyl-2-oxa-5-azabicyclo[2.2.2]octan-3-one structure having a hydroxyl group and a carboxyl group in the cis position is obtained.

The decarboxylation can proceed even by simply heating (simple heating) but the addition of an organic base such as triethylamine or pyridine promotes the reaction and enables the reaction to proceed at a low temperature so that it is preferable.

The reaction temperature of the decarboxylation by simple heating is typically 100° C. to 130° C., while it is typically 60° C. to 90° C. in cases where an organic base is added.

The reaction solvent is not particularly limited as long as it does not inhibit the reaction, but acetic acid or a mixed solvent of acetic acid and toluene is preferably used.

The amount of the organic base to be used is typically 0.1- to 2-fold, preferably 0.2- to 1-fold, relative to the amount of the lactonized compound (8) on the molar basis.

The reaction time is not particularly limited but is typically 1 to 12 hours and preferably 2 to 5 hours.

In the step 5(b), in the compound (8), the ester groups are hydrolyzed, one of the carboxyl groups is decarboxylated to form a stereoisomeric mixture of a 2-monocarboxylic acid, and then the stereoisomeric mixture is isomerized and lactonized to synthesize the compound represented by the formula (9) below:

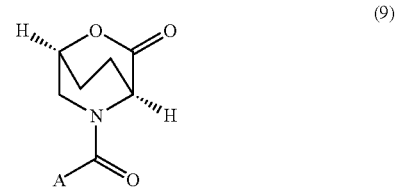

(wherein A represents an alkyl group containing 1 to 10 carbon atoms, an aryl group containing 6 to 12 carbon atoms, or an alkyloxy group containing 1 to 4 carbon atoms, an aralkyloxy group containing 7 to 20 carbon atoms).

In the step 5(b), the hydrolysis of the ester groups in the compound (8) can be performed under the same conditions as those in the step 5(a).

After the ester groups in the compound (8) are hydrolyzed, one of the carboxyl groups is decarboxylated to form a stereoisomeric mixture of a 2-monocarboxylic acid.

In the step 5(b), since decarboxylation is first performed, the dicarboxylic acid obtained by the ester degradation is first subjected to the decarboxylation to form a stereoisomeric mixture of a 2-monocarboxylic acid.

The decarboxylation can proceed even by simply heating (simple heating) but the addition of an organic base such as triethylamine or pyridine promotes the reaction and enables the reaction to proceed at a low temperature.

The reaction temperature of the decarboxylation by simple heating is typically 100° C. to 130° C., while it is typically 60° C. to 90° C. in cases where an organic base is added.

The reaction solvent is not particularly limited as long as it does not inhibit the reaction, but acetic acid or a mixed solvent of acetic acid and methanol is preferably used.

The amount of the organic base to be used is typically 0.1- to 2-fold, preferably 0.2- to 1-fold, relative to the amount of the compound (8), in which the ester groups have been hydrolyzed, on the molar basis.

The reaction time is not particularly limited but is typically 1 to 12 hours and preferably 2 to 5 hours.

Next, the stereoisomeric mixture is isomerized and lactonized. When the stereoisomeric mixture of the 2-monocarboxylic acid is isomerized and lactonized, a stereoisomer having the carboxyl group at position 2 in the cis position with respect to the hydroxyl group at position 5 is immediately lactonized with a dehydrating agent and a stereoisomer having the carboxyl group at position 2 in the trans position with respect to the hydroxyl group at position 5 is isomerized to the stereoisomer having the carboxyl group at position 2 in the cis position and then lactonized. Consequently, the compound (9) in the 5-acyl-2-oxa-5-azabicyclo[2.2.2]octan-3-one structure having a hydroxyl group and a carboxyl group in the cis position is eventually obtained from all types of the stereoisomers of the 2-monocarboxylic acid. Examples of an agent used in this step to perform dehydration and isomerization at the same time (a dehydrating and isomerizing/lactonizing agent) include acetic anhydride, a combination of acetic anhydride and an amine, trifluoroacetic anhydride, a combination of trifluoroacetic anhydride and an amine, a combination of a chlorocarbonate ester and an amine, and the like; and acetic anhydride or a combination of acetic anhydride and an amine is preferable among others.

The amount of the dehydrating and isomerizing/lactonizing agent to be used is typically 1- to 20-fold, preferably 1- to 5-fold, relative to the amount of the stereoisomeric mixture of the 2-monocarboxylic acid on the molar basis.

In cases where a combination with an amine is used, pyridine, triethylamine or like is used as the amine, and triethylamine is particularly preferable. The amount of the amine to be used is typically 0.1- to 3-fold, preferably 0.2- to 1-fold, relative to the amount of the stereoisomeric mixture of the 2-monocarboxylic acid on the molar basis.

The reaction temperature is not particularly limited but is typically 20° C. to 130° C. and preferably 60° C. to 90° C.

The reaction time is not particularly limited but is typically 1 to 12 hours and preferably 2 to 5 hours.

In the steps 5(a) and 5(b), the synthetic schemes can also be performed without isolation and purification during the course of synthesis from the dicarboxylic acid derived by the ester degradation to the compound (9).

In that case, for example, the compound (9) can be synthesized by dissolving a disodium salt of the dicarboxylic acid in acetic acid, adding acetic anhydride for the intramolecular lactone formation, then adding triethylamine and heating the mixture for the decarboxylation.

Moreover, for example, the compound (9) can also be synthesized by dissolving a disodium salt of the dicarboxylic acid in acetic acid, adding triethylamine followed by heating for the decarboxylation to form a stereoisomeric mixture of a 2-monocarboxylic acid, then adding acetic anhydride and heating the mixture. In this case, sodium acetate as a by-product can be deposited by addition of a poor solvent such as toluene and then removed by filtration.

In the step 5(a) or 5(b), in cases where A in the compound (9) to be synthesized is benzyloxy group, the compound is crystalline and therefore is isolated and purified by crystallization so that the compound (9) of high purity can be synthesized. Because (2S,5S)/(2R,5R)-5-hydroxypiperidine-2-carboxylic acid of high purity can be synthesized by performing the synthesis using the compound (9) of high purity, the compound (9) is particularly preferable as the synthetic intermediate. As the crystallization solvent, for example, a mixed solvent of toluene and heptane can be used.

Incidentally, A in the compound (9) is synonymous with A in the compound (5) described below.

Here, the compound (7) as a raw material can be synthesized by ordinary procedures of organic chemistry and is preferably synthesized by the steps (1) to (3) below.

The step 1 is a step of producing a compound represented by the formula (3) (the compound (3)) from a compound represented by the formula (1) (the compound (1)) as a raw material.

The hydroxyl group in a compound represented by the formula (1) below:

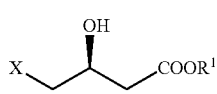

(1)

(wherein X represents Cl, Br, or I, and $R^1$ represents a hydrogen atom or an optionally substituted alkyl group containing 1 to 4 carbon atoms) is protected with a protecting group to synthesize a compound represented by the formula (2) below:

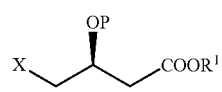

(2)

(wherein X represents Cl, Br, or I, $R^1$ represents a hydrogen atom or an optionally substituted alkyl group containing 1 to 4 carbon atoms, and P represents a protecting group) and then the ester group in the compound (2) is reduced to synthesize a compound represented by the formula (3) below:

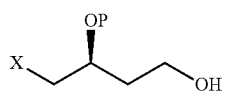

(3)

(wherein X represents Cl, Br, or I, and P represents a protecting group).

The compound (1) is a starting raw material of the step 1.

X in the formula (1) represents Cl, Br, or I, and X preferably represents Cl. $R^1$ represents a hydrogen atom or an optionally substituted alkyl group containing 1 to 4 carbon atoms, and $R^1$ preferably represents an optionally substituted alkyl group containing 1 to 4 carbon atoms. Examples of the alkyl group include, for example, methyl group, ethyl group, n-propyl group, isopropyl group, n-butyl group, isobutyl group, sec-butyl group, tert-butyl group, and the like. Examples of the substituent in the alkyl group include halogen atoms, alkoxy groups, and the like.

The compound (1) can easily be synthesized in accordance with a known method, for example, a method described in Tetrahedron: Asymmetry, 12(12), 1713 (2001) and the like. Moreover, a commercial product can be used as the compound (1) represented by the formula (1), in which X represents Cl or Br and $R^1$ represents a methyl group or ethyl group.

First, the hydroxyl group in the compound (1) is protected with a protecting group to synthesize the compound (2).

Ether protecting groups are preferable as the protecting group. It is the reason for the use of an ether protecting group that ether protecting groups are advantageous in the resistance to the basic conditions in the following steps. Incidentally, the oxygen atom binding to the protecting group P in the compound (2) is derived from the hydroxyl group.

Examples of the protecting group include tetrahydropyranyl group, methoxymethyl group, ethoxyethyl group, tert-butyl group, or tert-butyldimethylsilyl group. Those protecting groups can be introduced by protecting a hydroxyl group through the reaction with a combination of reaction agents, such as a combination of dihydropyran and an acid catalyst, methoxymethyl chloride and diisopropylethylamine, ethyl vinyl ether and an acid catalyst, isobutylene and an acid catalyst, and tert-butyldimethylsilyl chloride and imidazole, respectively. A preferable protecting group is tetrahydropyranyl group, methoxymethyl group, ethoxyethyl group, tert-butyl group, or tert-butyldimethylsilyl group. Among others, tetrahydropyranyl group is preferable as the protecting group because it has high safety.

In cases where tetrahydropyranyl group is used as the protecting group, for example, dihydropyran and an acid catalyst such as methanesulfonic acid, p-toluenesulfonic acid or pyridinium p-toluenesulfonate can be applied to the compound (1) in a reaction solvent to obtain the compound (2).

The reaction solvent is not particularly limited as long as the reaction is allowed to proceed, but toluene, heptane, dichloromethane, ethyl acetate and the like can be used. Moreover, the reaction can be allowed to proceed even in the absence of a solvent.

The amount of dihydropyran to be used is typically 1- to 10-fold, preferably 1- to 1.5-fold, relative to the amount of the compound (1) on the molar basis.

The amount of the acid catalyst to be used is typically 0.001- to 0.1-fold, preferably 0.002- to 0.02-fold, relative to the amount of the compound (1) on the molar basis.

The reaction temperature is not particularly limited but is typically 0° C. to 80° C. and preferably 20° C. to 60° C.

The reaction time is not particularly limited but is typically 0.5 to 10 hours and preferably 1 to 3 hours.

Moreover, X in the compound (2) represents Cl, Br, or I, and X preferably represents Cl.

In the compound (2), $R^1$ represents a hydrogen atom or an optionally substituted alkyl group containing 1 to 4 carbon atoms, and $R^1$ preferably represents an optionally substituted alkyl group containing 1 to 4 carbon atoms. Examples of the alkyl group include, for example, methyl group, ethyl group, n-propyl group, isopropyl group, n-butyl group, isobutyl group, sec-butyl group, tert-butyl group, and the like. Examples of the substituent in the alkyl group include halogen atoms, alkoxy groups, and the like.

In the compound (2), P represents a protecting group, preferably tetrahydropyranyl group, methoxymethyl group, ethoxyethyl group, tert-butyl group, or tert-butyldimethylsilyl group, and particularly preferably tetrahydropyranyl group.

Next, the ester group in the compound (2) is reduced to synthesize the compound (3).

In the reduction of the ester group in the compound (2) to alcohol, a hydride reducing agent is preferably used. For example, an aluminium hydride reducing agent such as lithium aluminium hydride, diisobutylaluminum hydride or sodium bis(methoxyethoxy)aluminium hydride, or a boron hydride reducing agent such as sodium borohydride, lithium borohydride, calcium borohydride or borane can be used. Among others, an aluminium hydride reducing agent or lithium borohydride is preferably used because of its high reaction activity in the reduction of esters.

For example, an aluminium hydride reducing agent can be applied to the compound (2) in a reaction solvent to synthesize the compound (3).

The reaction solvent is not particularly limited as long as the reaction is allowed to proceed, but tetrahydrofuran, toluene and the like can be used. Moreover, the reaction can be allowed to proceed even in the absence of a solvent.

The amount of the hydride reducing agent to be used is, in terms of hydride, typically 2- to 10-fold, preferably 2- to 3-fold, relative to the amount of the compound (2) on the molar basis.

The reaction temperature is not particularly limited but is typically 0° C. to 80° C. and preferably 0° C. to 20° C.

The reaction time is not particularly limited but is typically 0.5 to 10 hours and preferably 1 to 3 hours.

Incidentally, X and P in the compound (3) are synonymous with X and P in the compound (2).

The step 2 is a step of producing a compound represented by the formula (6) (the compound (6)) from the compound (3) as a raw material.

The hydroxyl group in the compound (3) is esterified with a sulfonate group to synthesize a compound represented by the formula (4) below:

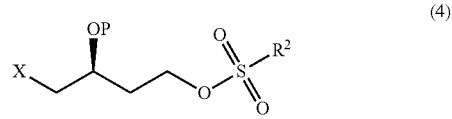

(wherein X represents Cl, Br, or I, $R^2$ represents an aryl group containing 6 to 12 carbon atoms, an alkyl group containing 1 to 10 carbon atoms, or an aralkyl group containing 7 to 20 carbon atoms)
and then the compound (4) is allowed to react with a compound represented by the formula (5) below:

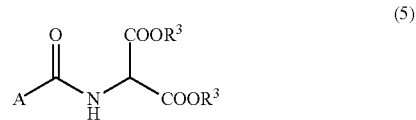

(wherein $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms)
to synthesize a compound represented by the formula (6) below:

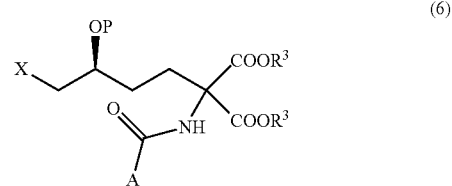

(wherein X represents Cl, Br, or I, P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

First, the hydroxyl group in the compound (3) is esterified with a sulfonate group to synthesize the compound (4).

In the esterification of the hydroxyl group in the compound (3) with a sulfonate group, a combination of a commonly used alkylsulfonyl chloride and a base, or a combination of a commonly used arylsulfonyl chloride and a base can be employed. For example, a combination of methanesulfonyl chloride or p-toluenesulfonyl chloride and triethylamine can be employed.

For example, an alkylsulfonyl chloride or arylsulfonyl chloride and a base can be applied to the compound (3) in a reaction solvent to synthesize the compound (4).

The reaction solvent is not particularly limited as long as the reaction is allowed to proceed, but toluene, methylene chloride, tetrahydrofuran, ethyl acetate and the like can be used. Moreover, the reaction can be allowed to proceed even in the absence of a solvent.

Moreover, an organic base such as pyridine or triethylamine, or an inorganic base such as sodium bicarbonate or sodium hydroxide can be used as the base.

The amount of the alkylsulfonyl chloride or arylsulfonyl chloride to be used is typically 1- to 2-fold, preferably 1- to 1.2-fold, relative to the amount of the compound (3) on the molar basis.

The amount of the base to be used is typically 1- to 2-fold, preferably 1- to 1.5-fold, relative to the amount of the compound (3) on the molar basis.

The reaction temperature is not particularly limited but is typically 0° C. to 50° C. and preferably 0° C. to 20° C.

The reaction time is not particularly limited but is typically 0.5 to 5 hours and preferably 1 to 2 hours.

Incidentally, X and P in the compound (4) are synonymous with X and P in the compound (2).

Moreover, in the compound (4), $R^2$ represents an aryl group containing 6 to 12 carbon atoms, an alkyl group containing 1 to 10 carbon atoms, or an aralkyl group containing 7 to 20 carbon atoms, preferably represents an aryl group containing 6 to 7 carbon atoms, an alkyl group containing 1 to 3 carbon atoms, or an aralkyl group containing 7 to 11 carbon atoms, and more preferably represents a methyl group. Examples of the aryl group include, for example, phenyl group, tolyl group, naphthyl group, biphenyl group, and the like. Examples of the alkyl group include, for example, methyl group, ethyl group, n-propyl group, isopropyl group, n-butyl group, isobutyl group, sec-butyl group, tert-butyl group, pentyl group, hexyl group, heptyl group, octyl group, and the like. Examples of the aralkyl group include, for example, benzyl group, phenethyl group, and the like.

Next, the compound (4) is allowed to react with compound (5) to synthesize the compound (6).

In the compound (5), $R^3$ represents an alkyl group containing 1 to 4 carbon atoms, and preferably an alkyl group containing 1 to 2 carbon atoms. Examples of the alkyl group include, for example, methyl group, ethyl group, n-propyl group, isopropyl group, n-butyl group, isobutyl group, sec-butyl group, tert-butyl group, and the like.

Moreover, in the compound (5), A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms, preferably represents an aryl group containing 6 to 10 carbon atoms, an alkyl group containing 1 to 3 carbon atoms, an alkyloxy group containing 1 to 4 carbon atoms, or an aralkyloxy group containing 7 to 11 carbon atoms, and more preferably represents a methyl group. Examples of the aryl group include, for example, phenyl group, naphthyl group, biphenyl group, and the like. Examples of the alkyl group include, for example, methyl group, ethyl group, n-propyl group, isopropyl group, n-butyl group, isobutyl group, sec-butyl group, tert-butyl group, pentyl group, hexyl group, heptyl group, octyl group, and the like. Examples of the alkyloxy group include methyloxy group, ethyloxy group, n-propyloxy group, isopropyloxy group, n-butyloxy group, isobutyloxy group, tert-butyloxy group, and the like. Examples of the aralkyloxy group include benzyloxy group, phenethyloxy group, and the like.

A commercial product can be used as the compound (5). A compound (5) can be available, for example, from TateyamaKasei Co., Ltd.

When the reaction between the compound (4) and the compound (5) is performed, a base is necessary to generate an anion at the α-position in the compound (5). For this purpose, the reaction is preferably performed in the presence of, for example, a strong base such as sodium hydride, sodium hexamethyldisilazane, lithium hexamethyldisilazane, lithium diisopropylamide, sodium tert-butoxide, potassium tert-butoxide, sodium ethoxide, sodium methoxide, sodium hydroxide, or potassium hydroxide; or a weak base such as cesium carbonate, potassium carbonate, or sodium carbonate. The reaction is preferably performed in the presence of a base, such as, among others, sodium hydride, sodium tert-butoxide, potassium tert-butoxide, sodium ethoxide, cesium carbonate or potassium carbonate.

The amount of the base to be used is typically not less than 0.8-fold, preferably 0.8- to 1.2-fold in cases of a strong base and 0.8- to 3-fold in cases of a weak base, relative to the amount of the substrate (the compound (5)) on the molar basis.

The reaction solvent is not particularly limited as long as it can dissolve the substrate, but aprotic polar solvents such as dimethylsulfoxide, N,N-dimethylformamide, N,N-dimethylacetamide, N-methylpyrrolidone and the like; alcohol solvents such as methanol, ethanol, propanol, butanol and the like; ether solvents such as tetrahydrofuran, diethyl ether, methyl-tert-butyl ether, methylcyclopropyl ether and the like; and mixed solvents thereof with a hydrocarbon solvent such as toluene, hexane, or heptane, or with a halohydrocarbon solvent such as dichloromethane, chloroform, or 1,2-dichloroethane are preferably used. Even more preferably, dimethylsulfoxide, N,N-dimethylformamide, N-methylpyrrolidone, tetrahydrofuran, mixed solvents thereof with toluene, a mixed solvent of ethanol and toluene are used.

The reaction temperature is not particularly limited but is typically 0° C. to 130° C. and preferably 20° C. to 80° C.

The reaction time is not particularly limited but is typically for 1 to 24 hours and preferably 1 to 5 hours.

In this step, an iodide salt is preferably added for the purpose of promoting the reaction and increasing the selectivity. As examples of the iodide salt, iodide salts represented by MI (M refers to an alkali metal) are preferable and, among others, iodide salts such as potassium iodide, sodium iodide and the like are preferable. The amount of these salts to be added is 0.02- to 1-fold, preferably 0.2- to 0.4-fold, relative to the amount of the substrate (the compound (4)) on the molar basis.

The amount of the compound (5) to be used for the compound (4) is 1- to 2-fold, preferably 1- to 1.2-fold, relative to the amount of the compound (4) on the molar basis.

Incidentally, in the compound (6), X and P are synonymous with X and P in the compound (2), and $R^3$ and A are synonymous with $R^3$ and A in the compound (5).

The step 3 is a step of producing a compound represented by the formula (7) (the compound (7)) from the compound (6) as a raw material.

The compound (6) is cyclized to synthesize a compound represented by the formula (7) below:

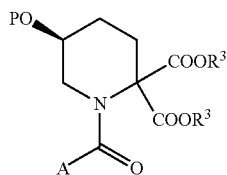

(7)

(wherein P represents a protecting group, R³ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

A base is required in the step 3. As the base, for example, a strong base such as sodium hydride, sodium hexamethyldisilazane, lithium hexamethyldisilazane, lithium diisopropylamide, sodium tert-butoxide, potassium tert-butoxide, sodium ethoxide, sodium methoxide, sodium hydroxide, or potassium hydroxide; or a weak base such as cesium carbonate, potassium carbonate, or sodium carbonate is used, and sodium hydride, sodium tert-butoxide, potassium tert-butoxide, cesium carbonate or potassium carbonate is preferably used.

The amount of the base to be used is typically not less than 1-fold, preferably 1- to 2-fold in cases of a strong base and 1- to 3-fold in cases of a weak base, relative to the amount of the substrate (the compound (6)) on the molar basis.

The reaction solvent is not particularly limited as long as it can dissolve the substrate (the compound (6)), but aprotic polar solvents such as dimethylsulfoxide, N,N-dimethylformamide, N,N-dimethylacetamide, N-methylpyrrolidone or the like; or ether solvents such as tetrahydrofuran, diethyl ether, methyl-tert-butyl ether, methylcyclopropyl ether and the like; and mixed solvents thereof with a hydrocarbon solvent such as toluene, hexane, or heptane, or with a halohydrocarbon solvent such as dichloromethane, chloroform, or 1,2-dichloroethane are preferably used, and N,N-dimethylformamide, N-methylpyrrolidone, tetrahydrofuran, and mixed solvents thereof with toluene are even more preferably used.

The reaction temperature is not particularly limited but is typically 0° C. to 130° C., preferably 10° C. to 50° C. in cases of a strong base, and preferably 80° C. to 130° C. in cases of a weak base.

The reaction time is not particularly limited but is typically for 1 to 24 hours and preferably 1 to 6 hours.

This step is preferably performed in the presence of a quaternary ammonium salt such as tetrabutylammonium bromide and the like for the purpose of promoting the reaction and increasing the selectivity. The amounts of these salts to be used are 0.02- to 1-fold, preferably 0.2- to 0.4-fold, relative to the amount of the substrate (the compound (6)) on the molar basis.

Moreover, the step 2 and the step 3 can also be performed in series without isolation and purification of the compound (6) during the course of synthesis. In that case, the step 3 can be performed by adding a base to the reaction mixture after the reaction of the step 2 has been completed.

Incidentally, in the compound (7), P is synonymous with P in the compound (2), and R³ and A are synonymous with R³ and A in the compound (5).

In the present invention, (2S,5S)/(2R,5R)-5-hydroxypiperidine-2-carboxylic acid is preferably synthesized with the following step 6.

The step 6 is a step of producing a compound represented by the formula (10) (the compound (10)) from the compound (9) as a raw material.

The lactone in the compound (9) is hydrolyzed and the amide bond in the compound (9) is cleaved to synthesize (2S,5S)/(2R,5R)-5-hydroxypiperidine-2-carboxylic acid represented by the formula (10) below:

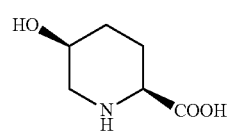

(10)

The hydrolysis of the lactone and the cleavage of the amide bond in the compound (9) may be allowed to proceed at the same time.

Commonly used conditions can be employed in the cleavage of the amide bond. For example, in cases where A is an alkyl group or aryl group, the cleavage can easily be achieved by applying a strong acid as a catalyst, such as hydrochloric acid, hydrobromic acid and the like, in a reaction solvent.

As the reaction solvent, water, or aqueous solvents such as aqueous dioxane, aqueous dimethoxyethane, aqueous acetone and the like are used.

The amount of the strong acid to be used is typically 1- to 10-fold, preferably 1- to 2-fold, relative to the amount of the compound (9) on the molar basis.

The reaction temperature is not particularly limited but is typically 0° C. to 100° C. and preferably 80° C. to 100° C.

The reaction time is not particularly limited but is typically 1 to 12 hours and preferably 3 to 6 hours.

In the hydrolysis of the lactone, an acid or a base, for example, hydrochloric acid or sodium hydroxide is used in accordance with a commonly employed hydrolysis procedure.

As the reaction solvent, water, methanol, ethanol and the like are used.

The amount of the acid or base to be used is typically 1- to 10-fold, preferably 1- to 2-fold, relative to the amount of the compound (9) after the cleavage of the amide bond on the molar basis.

The reaction temperature is not particularly limited but is typically 0° C. to 100° C. and preferably 60° C. to 100° C.

The reaction time is not particularly limited but is typically 1 to 12 hours and preferably 8 to 12 hours.

In the step 6, in cases where the compound (9) is a compound represented by the formula (9a):

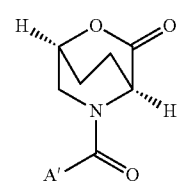

(9a)

(wherein A' represents an alkyl group containing 1 to 10 carbon atoms or an aryl group containing 6 to 12 carbon atoms), for example, the addition of hydrochloric acid followed by heating enables the hydrolysis of the lactone and the acetyl group to be performed at the same time.

In this case, because the resulting (2S,5S)/(2R,5R)-5-hydroxypiperidine-2-carboxylic acid is a hydrochloride, the removal of hydrochloric acid and the like can be achieved with ion exchange resins in accordance with a commonly employed procedure for the purification of amino acids. Moreover, the hydrochloric acid is neutralized using lithium hydroxide or lithium carbonate to produce lithium chloride, or alternatively using triethylamine to produce triethylamine hydrochloride. Then the reaction mixture is concentrated and followed by the addition of an alcohol, acetone and the like, so that the lithium chloride and triethylamine hydrochloride can be removed.

Incidentally, in the compound (9a), A' represents an alkyl group containing 1 to 10 carbon atoms or an aryl group containing 6 to 10 carbon atoms, and preferably represents an alkyl group containing 1 to 3 carbon atoms or an aryl group containing 6 carbon atoms. Examples of the aryl group include, for example, phenyl group. Examples of the alkyl group include, for example, methyl group, ethyl group, n-propyl group, isopropyl group, n-butyl group, isobutyl group, sec-butyl group, tert-butyl group, pentyl group, hexyl group, heptyl group, octyl group, and the like.

Moreover, because (2S,5S)/(2R,5R)-5-hydroxypiperidine-2-carboxylic acid is crystalline, it can be purified by performing recrystallization. As the recrystallization solvent, for example, a water/ethanol mixed system, a methanol/acetone mixed system and the like can be used.

In the steps 1 to 5 of the present invention, it is preferable in the compounds (1) to (9) that X represents Cl, $R^1$ and $R^3$ represent an ethyl group, $R^2$ represents a methyl group or p-tolyl group, A represents a methyl group or phenyl group, and P represents a tetrahydropyranyl group or methoxymethyl group, ethoxyethyl group, tert-butydimethylsilyl group or tert-butyl group.

In the present invention, (2S,5S)/(2R,5R)-5-hydroxypiperidine-2-carboxylic acid is preferably produced by coupling the sulfonate ester of an optically active 4-halo-3-protected hydroxybutanol (the compound (4)), which is derived from an optically active 4-halo-3-hydroxybutanoate ester (the compound (1)), to an acylaminomalonate diester (the compound (5)) to obtain an optically active 2-acylamino-2-[4-halo-3-protected hydroxybutyl]-malonate diester (the compound (6)); performing cyclization and deprotection on it to obtain an optically active 1-acyl-5-hydroxypiperidine-2,2-dicarboxylate diester (the compound (8)); and then hydrolyzing the ester, followed by (a) forming a lactone from the hydroxyl group at position 5 and one of the dicarboxylates at position 2, and decarboxylating the remaining carboxylate, or (b) decarboxylating to form a stereoisomeric mixture of a 2-monocarboxylic acid, and isomerizing and lactonizing the 2-monocarboxylic acid, to obtain 5-acyl-2-oxa-5-azabicyclo[2.2.2]octan-3-one (the compound (9)); and finally performing deprotection and hydrolysis. Accordingly the optically active substances can be efficiently synthesized.

[2] Novel Compounds

The present invention relates to the novel compounds indicated below. These novel compounds are useful as synthetic intermediates for a β-lactamase inhibitor and the like.

The novel compounds of the present invention can be produced by the production method of the present invention.

Moreover, they can also be synthesized by ordinary procedures of organic chemistry since this specification has indicated the structures thereof.

(A) Compounds Represented by the Formula (2a) Below:

(2a)

(wherein X represents Cl, Br, or I, $R^1$ represents a hydrogen atom or an optionally substituted alkyl group containing 1 to 4 carbon atoms, P''' represents a tetrahydropyranyl group or ethoxyethyl group).

X represents Cl, Br, or I, and preferably Cl.

$R^1$ represents a hydrogen atom or an optionally substituted alkyl group containing 1 to 4 carbon atoms, and preferably an optionally substituted alkyl group containing 1 to 4 carbon atoms. Examples of the alkyl group include, for example, methyl group, ethyl group, n-propyl group, isopropyl group, n-butyl group, isobutyl group, sec-butyl group, tert-butyl group, and the like. Examples of the substituent in the alkyl group include halogen atoms, alkoxy groups, and the like.

P''' represents a tetrahydropyranyl group, or ethoxyethyl group.

Among the compounds (2a), compounds represented by the formulae below are particularly preferable:

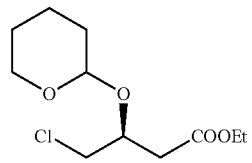

(2b)

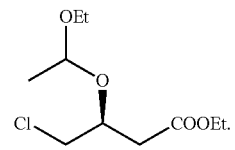

(2d)

(B) Compounds Represented by the Formula (3a) Below:

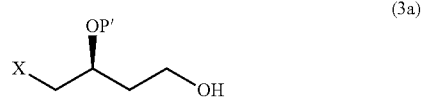

(3a)

(wherein X represents Cl, Br, or I, and P' represents a tetrahydropyranyl group, methoxymethyl group, ethoxyethyl group, tert-butyl group, or tert-butyldimethylsilyl group).

P' represents a tetrahydropyranyl group, methoxymethyl group, ethoxyethyl group, tert-butyl group, or tert-butyldimethylsilyl group.

Incidentally, in the compounds (3a), X is synonymous with X in the compound (2a).

Among the compounds (3a), compounds represented by the formulae below are particularly preferable:

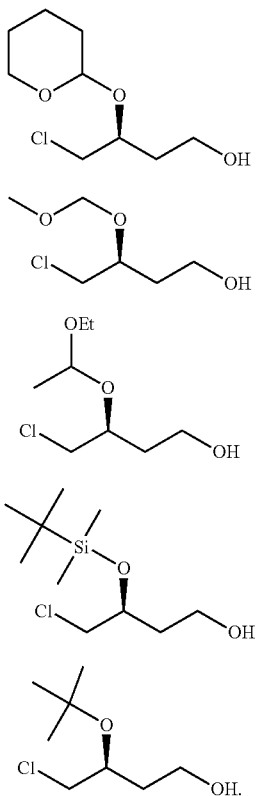

(C) Compounds Represented by the Formula (4a) Below:

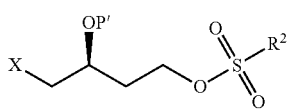

(wherein X represents Cl, Br, or I, P' represents a tetrahydropyranyl group, methoxymethyl group, ethoxyethyl group, tert-butyl group, or tert-butyldimethylsilyl group, and $R^2$ represents an aryl group containing 6 to 12 carbon atoms, an alkyl group containing 1 to 10 carbon atoms, or an aralkyl group containing 7 to 20 carbon atoms).

$R^2$ represents an aryl group containing 6 to 12 carbon atoms, an alkyl group containing 1 to 10 carbon atoms, or an aralkyl group containing 7 to 20 carbon atoms, preferably represents an aryl group containing 6 to 7 carbon atoms, an alkyl group containing 1 to 3 carbon atoms, or an aralkyl group containing 7 to 11 carbon atoms, and more preferably represents a methyl group. Examples of the aryl group include, for example, phenyl group, tolyl group, naphthyl group, biphenyl group, and the like. Examples of the alkyl group include, for example, methyl group, ethyl group, n-propyl group, isopropyl group, n-butyl group, isobutyl group, sec-butyl group, tert-butyl group, pentyl group, hexyl group, heptyl group, octyl group, and the like. Examples of the aralkyl group include, for example, benzyl group, phenethyl group, and the like.

Incidentally, in the compounds (4a), X is synonymous with X in the compound (2a) and P' is synonymous with P' in the compound (3a).

Among the compounds (4a), compounds represented by the formulae below are particularly preferable:

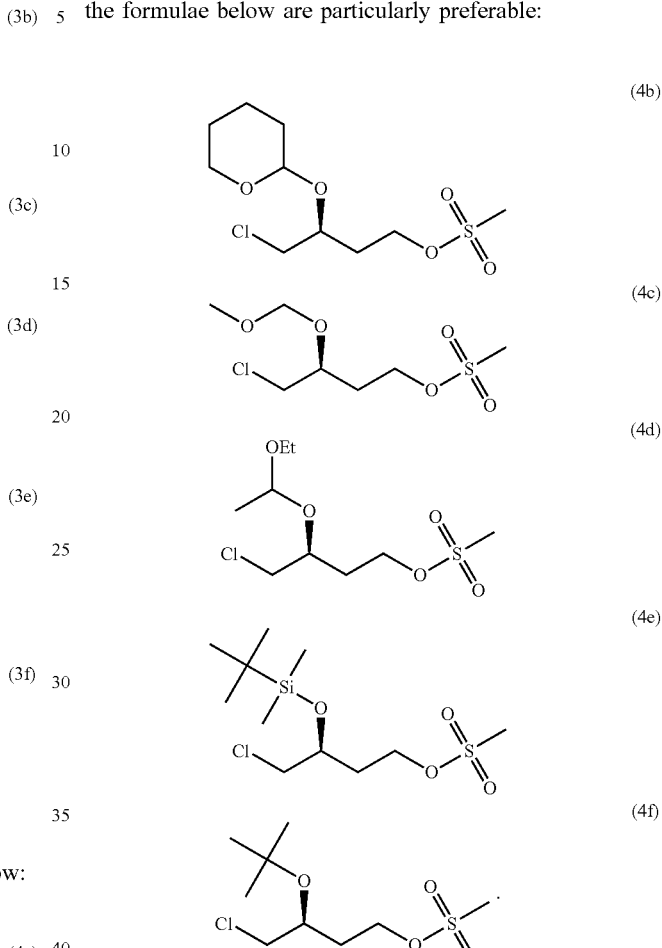

(D) Compounds Represented by the Formula (6a) Below:

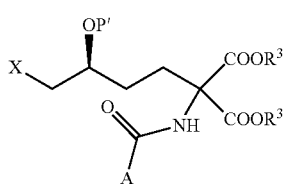

(wherein X represents Cl, Br, or I, P' represents a tetrahydropyranyl group, methoxymethyl group, ethoxyethyl group, tert-butyl group, or tert-butyldimethylsilyl group, and $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

$R^3$ represents an alkyl group containing 1 to 4 carbon atoms, and preferably an alkyl group containing 1 to 2 carbon atoms. Examples of the alkyl group include, for example, methyl group, ethyl group, n-propyl group, isopropyl group, n-butyl group, isobutyl group, sec-butyl group, tert-butyl group, and the like.

A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms, preferably represents an alkyl group containing 1 to 3 carbon atoms, an aryl group containing 6 to 10 carbon atoms, an alkyloxy group containing 1 to 4 carbon atoms, or an aralkyloxy group containing 7 to 11 carbon atoms, and more preferably represents a methyl group and phenyl group. Examples of the aryl group include, for example, phenyl group, naphthyl group, biphenyl group, and the like. Examples of the alkyl group include, for example, methyl group, ethyl group, n-propyl group, isopropyl group, n-butyl group, isobutyl group, sec-butyl group, tert-butyl group, pentyl group, hexyl group, heptyl group, octyl group, and the like. Examples of the alkyloxy group include methyloxy group, ethyloxy group, n-propyloxy group, isopropyloxy group, n-butyloxy group, isobutyloxy group, tert-butyloxy group, and the like. Examples of the aralkyloxy group include benzyloxy group, phenethyloxy group, and the like.

Incidentally, in the compounds (6a), X is synonymous with X in the compound (2a) and P' is synonymous with P' in the compound (3a).

Among the compounds (6a), compounds represented by the formulae below are particularly preferable:

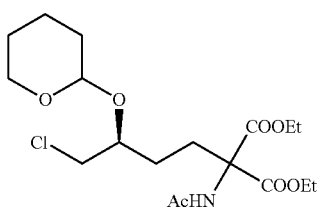
(6b)

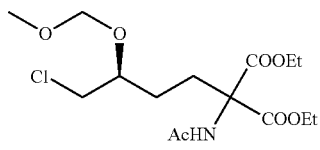
(6c)

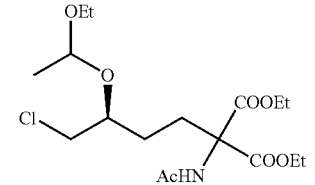
(6d)

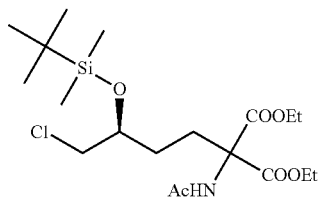
(6e)

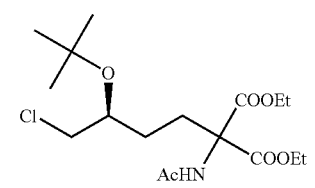
(6f)

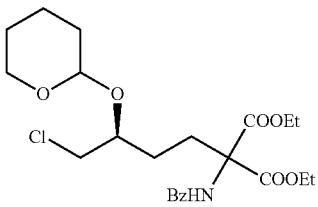
(6g)

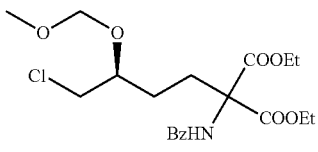
(6h)

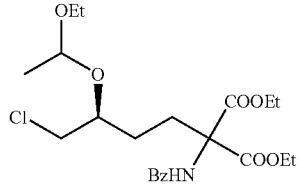
(6i)

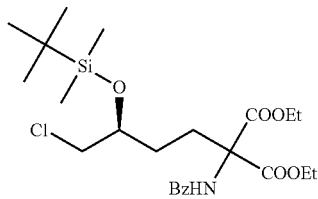
(6j)

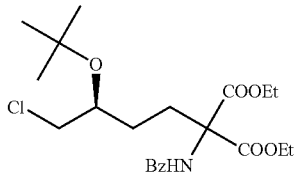
(6k)

(wherein Ac represents an acetyl group and Bz represents a benzoyl group).

(E) Compounds represented by the formula (7) below:

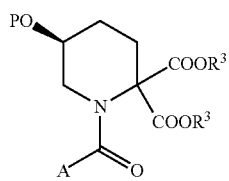
(7)

(wherein P represents a protecting group, $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms or an aralkyloxy group containing 7 to 20 crbon atoms).

P represents a protecting group and preferably represents a tetrahydropyranyl group, methoxymethyl group, ethoxyethyl group, tert-butyl group, or tert-butyldimethylsilyl group.

Incidentally, in the compounds (7), $R^3$ and A are synonymous with $R^3$ and A in the compound (6a).

Among the compounds (7), compounds represented by the formulae below are particularly preferable:

(7a) [structure: tetrahydropyranyl-O-piperidine with Ac on N and two COOEt groups]

(7b) [structure: MOM-O-piperidine with Ac on N and two COOEt groups]

(7c) [structure: CH(OEt)-O-piperidine with Ac on N and two COOEt groups]

(7d) [structure: TBDMS-O-piperidine with Ac on N and two COOEt groups]

(7e) [structure: t-Bu-O-piperidine with Ac on N and two COOEt groups]

(7f) [structure: tetrahydropyranyl-O-piperidine with Bz on N and two COOEt groups]

(7g) [structure: MOM-O-piperidine with Bz on N and two COOEt groups]

(7h) [structure: CH(OEt)-O-piperidine with Bz on N and two COOEt groups]

(7i) [structure: TBDMS-O-piperidine with Bz on N and two COOEt groups]

(7j) [structure: t-Bu-O-piperidine with Bz on N and two COOEt groups]

(wherein Ac represents an acetyl group and Bz represents a benzoyl group).

(F) Compounds Represented by the Formula (8) Below or Dicarboxylic Acid Salts Thereof:

(8) [structure: HO-piperidine with N-acyl (A-C(=O)-) and two COOR³ groups]

(wherein $R^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms).

Incidentally, in the compounds (8), $R^3$ and A are synonymous with $R^3$ and A in the compound (6a).

Among the compounds (8), compounds represented by the formulae below are particularly preferable:

(8a) [structure: HO-piperidine with Ac on N and two COOEt groups]

(8b) [structure: HO-piperidine with Bz on N and two COOEt groups]

(wherein Ac represents an acetyl group and Bz represents a benzoyl group).

Among these, the compound (8a) is preferable as a synthetic intermediate since it is crystalline and thus can be isolated and purified by crystallization.

(G) Compounds Represented by the Formula (9a) Below:

(9a) [bicyclic lactone structure with N-acyl group A'-C(=O)-]

(wherein A' represents an alkyl group containing 1 to 10 carbon atoms or an aryl group containing 6 to 12 carbon atoms).

A' represents an alkyl group containing 1 to 10 carbon atoms or an aryl group containing 6 to 12 carbon atoms, and preferably represents an alkyl group containing 1 to 3 carbon atoms or an aryl group containing 6 carbon atoms. Examples of the alkyl group include, for example, methyl group, ethyl group, n-propyl group, isopropyl group, n-butyl group, isobutyl group, sec-butyl group, tert-butyl group, pentyl group, hexyl group, heptyl group, octyl group, and the like. Examples of the aryl group include phenyl group, naphthyl group and the like.

Among the compounds (9a), compounds represented by the formulae below are particularly preferable:

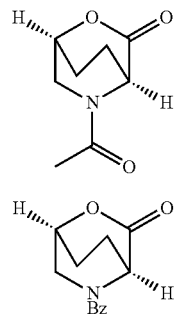

(9b)

(9c)

(wherein Ac represents an acetyl group and Bz represents a benzoyl group).

(H) A Compound or a Salt Thereof, the Compound Represented by the Formula (11a) Below:

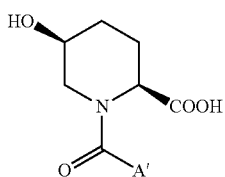

(11a)

(wherein A' represents an alkyl group containing 1 to 10 carbon atoms or an aryl group containing 6 to 12 carbon atoms)

or the formula (11b) below:

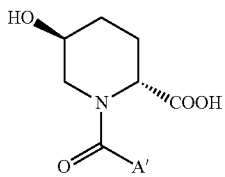

(11b)

(wherein A' represents an alkyl group containing 1 to 10 carbon atoms or an aryl group containing 6 to 12 carbon atoms).

Incidentally, in the compounds (11a) and (11b), A' is synonymous with A' in the compound (9a).

Among the compounds (11a) or (11b), compounds represented by the formulae below are particularly preferable:

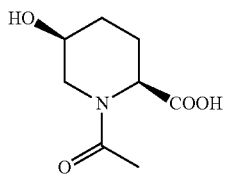

(11c)

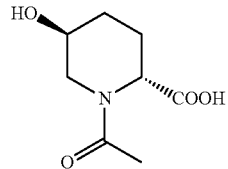

(11d)

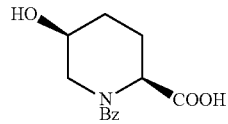

(11e)

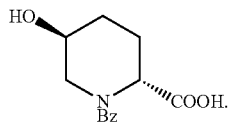

(11f)

EXAMPLES

Now, the present invention will be described in further detail by way of Examples but the present invention is not limited by these Examples.

[Example 1] Production of (3S)-4-chloro-3-(tetrahydropyran-2-yloxy)-butan-1-ol (a Compound of the Formula (3), Wherein X=Cl, and P=Tetrahydropyranyl Group)

In a 50-mL reactor, 1.50 g (9 mmol) of ethyl (3S)-4-chloro-3-hydroxybutanoate ester (a compound of the formula (1), wherein X=Cl, and $R^1$=ethyl group), 1.51 g (18 mmol) of dihydropyran, 29 μL (0.45 mmol) of methanesulfonic acid and 15 mL of toluene were placed and the mixture was stirred for 0.5 hour at room temperature, followed by the addition of 250 μL (1.8 mmol) of triethylamine to stop the reaction. This mixture was washed with water, dried, and then concentrated to obtain 3.14 g of an oily crude ethyl (3S)-4-chloro-3-(tetrahydropyran-2-yloxy)-butanoate ester (a compound of the formula (2), wherein X=Cl, P=tetrahydropyranyl group, and $R^1$=ethyl group).

$^1$H-NMR (400 MHz, $CDCl_3$) δ1.23 (3H, m), 1.44-1.85 (6H, m), 2.58-2.80 (2H, m), 3.47-3.95 (4H, m), 4.17 (2H, m), 4.20-4.37 (1H, m), 4.73-4.80 (1H, m).

Next, the obtained crude ethyl (3S)-4-chloro-3-(tetrahydropyran-2-yloxy)-butanoate ester (a compound of the formula (2), wherein X=Cl, P=tetrahydropyranyl group, and $R^1$=ethyl group) was dissolved in 15 mL of dry tetrahydrofuran (hereinafter referred to as "THF"), and 0.34 g (9 mmol) of lithium aluminium hydride was added thereto and the mixture was stirred for 2 hours at 5° C., followed by the addition of 1 mL of ethyl acetate and then 1 mL of water to degrade an excess amount of the reducing agent and stop the reaction. This mixture was filtered through Celite and purified by silica gel column chromatography to obtain 1.43 g of an oil of (3S)-4-chloro-3-(tetrahydropyran-2-yloxy)-butan-1-ol (a compound of the formula (3), wherein X=Cl, and P=tetrahydropyranyl group) (the total yield through the two steps: 73%).

$^1$H-NMR (400 MHz, $CDCl_3$) δ1.45-2.08 (8H, m), 3.35-4.13 (8H, m), 4.68-4.76 (1H, m).

[Example 2] Production of (3S)-4-chloro-3-(tetrahydropyran-2-yloxy)-butyl methanesulfonate Ester (a Compound of the Formula (4), Wherein X=Cl, P=Tetrahydropyranyl Group, and R²=Methyl Group)

In a 50-mL reactor, 1.43 g (6.8 mmol) of the (3S)-4-chloro-3-(tetrahydropyran-2-yloxy)-butan-1-ol (a compound of the formula (3), wherein X=Cl, and P=tetrahydropyranyl group) obtained in Example 1, 1.05 mL (7.5 mmol) of triethylamine and 14 mL of toluene were placed, and 0.56 mL (7.18 mmol) of methanesulfonyl chloride was added thereto at 5° C. and the mixture was stirred for 1 hour at 5° C. This reaction liquid was washed with water, dried, and then concentrated to obtain 2.13 g of an oily crude (3S)-4-chloro-3-(tetrahydropyran-2-yloxy)-butyl methanesulfonate ester (a compound of the formula (4), wherein X=Cl, P=tetrahydropyranyl group, and R²=methyl group) (yield: 97%).

$^1$H-NMR (400 MHz, CDCl$_3$) δ1.48-1.60 (4H, m), 1.72-1.85 (2H, m), 1.97-2.20 (2H, m), 3.02 (3H, s), 3.50-4.12 (5H, m), 4.30-4.45 (2H, m), 4.68 (1H, m).

[Example 3] Production of (3S)-4-chloro-3-(tetrahydropyran-2-yloxy)-butyl methanesulfonate Ester (a Compound of the Formula (4), Wherein X=Cl, P=Tetrahydropyranyl Group, and R²=Methyl Group)

In a 1-L reactor, 30 g (180.18 mmol) of ethyl (3S)-4-chloro-3-hydroxybutanoate ester (a compound of the formula (1), wherein X=Cl, and R¹=ethyl group), 18.16 g (216.22 mmol) of dihydropyran, 0.44 g (1.80 mmol) of pyridinium p-toluenesulfonate and 240 mL of toluene were placed and the mixture was stirred for 10 hours at 45° C. to obtain a solution of ethyl (3S)-4-chloro-3-(tetrahydropyran-2-yloxy)-butanoate ester (a compound of the formula (2), wherein X=Cl, P=tetrahydropyranyl group, and R¹=ethyl group) in toluene.

Then, 70 mL (252.25 mmol) of a 70% solution of sodium bis(methoxyethoxy)aluminium hydride in toluene was added to this reaction liquid at 5° C. to 10° C. and the mixture was stirred for 7 hours at 5° C. to 10° C. To this reaction liquid, 22.7 mL of water, 31.59 g of magnesium sulfate, and 22.7 mL of water were added sequentially at 5° C. to 10° C. and the mixture was stirred for 1 hour at 5° C. to 10° C. and left to stand overnight at 5° C., followed by the filtration of solids. Then, the filtrate was washed with saturated brine, dried, and subsequently concentrated to obtain 247.39 g of (3S)-4-chloro-3-(tetrahydropyran-2-yloxy)-butan-1-ol (a compound of the formula (3), wherein X=Cl, and P=tetrahydropyranyl group) in toluene solution (the total yield through the two steps: 91%).

Next, to 237.3 g of this solution (containing 32.59 g (156.33 mmol) of (3S)-4-chloro-3-(tetrahydropyran-2-yloxy)-butan-1-ol (a compound of the formula (3), wherein X=Cl, and P=tetrahydropyranyl group)), 17.37 g (171.96 mmol) of triethylamine was added and then 18.79 g (164.15 mmol) of methanesulfonyl chloride was added thereto at 5° C. to 12° C. and the mixture was stirred for 1 hour at 5° C. to 10° C. This reaction liquid was washed with water, dried, and then concentrated to obtain 51.72 g (pure content: 43.92 g) of crude (3S)-4-chloro-3-(tetrahydropyran-2-yloxy)-butyl methanesulfonate ester (a compound of the formula (4), wherein X=Cl, P=tetrahydropyranyl group, and R²=methyl group) (the total yield through the three steps: 89%).

[Example 4-1] Production of (3S)-4-chloro-3-methoxymethyloxy-butyl methanesulfonate Ester (a Compound of the Formula (4), Wherein X=Cl, P=Methoxymethyl Group, and R²=Methyl Group)

In a 50-mL reactor, 1.50 g (9.01 mmol) of ethyl (3S)-4-chloro-3-hydroxybutanoate ester (a compound of the formula (1), wherein X=Cl, and R¹=ethyl group), 2.02 mL (11.71 mmol) of diisopropylethylamine and 15 mL of toluene were placed and 1.18 g (11.71 mmol) of methoxymethyl chloride was added thereto at room temperature and the mixture was stirred at room temperature. After the completion of the reaction, the reaction liquid was washed with water, dried, and then concentrated to obtain 2.54 g of crude ethyl (3S)-4-chloro-3-methoxymethyloxy-butanoate ester (a compound of the formula (2), wherein X=Cl, P=methoxymethyl group, and R¹=ethyl group).

$^1$H-NMR (400 MHz, CDCl$_3$) δ1.26 (3H, t, J=7.6 Hz), 2.60-2.75 (2H, m), 3.38 (3H, s), 3.67 (2H, d, J=5.2 Hz), 4.15 (2H, q, J=7.3 Hz), 4.23 (1H, m), 4.71 (2H, dd, J=6.8, 22 Hz).

Next, 2.54 g of this crude ethyl (3S)-4-chloro-3-methoxymethyloxy-butanoate ester (a compound of the formula (2), wherein X=Cl, P=methoxymethyl group, and R¹=ethyl group) was dissolved in 14 mL of toluene, and then 2.75 mL (9.91 mmol) of a 70% solution of sodium bis(methoxyethoxy)aluminium hydride in toluene was added thereto at 5° C. to 10° C. and the mixture was stirred for 1 hour at 5° C. to 10° C. To this reaction liquid, 1.8 mL of water, 0.56 g of sodium sulfate, and 0.68 g of magnesium sulfate were added sequentially at 5° C. to 10° C., and the mixture was stirred for 1 hour at 5° C. to 10° C. and filtered to remove solids. Then, the filtrate was washed with saturated brine, dried, and subsequently concentrated to obtain a solution of (3S)-4-chloro-3-methoxymethyloxy-butan-1-ol (a compound of the formula (3), wherein X=Cl, P=methoxymethyl group) in toluene.

$^1$H-NMR (400 MHz, CDCl$_3$) δ1.78-1.95 (2H, m), 3.43 (3H, s), 3.58-3.67 (2H, m), 3.98 (1H, m), 4.74 (2H, dd, J=7.2, 24 Hz).

Next, 1.57 mL (11.29 mmol) of triethylamine was added to this solution and then 0.83 mL (10.72 mmol) of methanesulfonyl chloride was added thereto at 5° C. to 10° C. and the mixture was stirred for 1 hour at 5° C. to 10° C. This reaction liquid was washed with water, dried, and then concentrated to obtain 1.39 g of (3S)-4-chloro-3-methoxymethyloxy-butyl methanesulfonate ester (a compound of the formula (4), wherein X=Cl, P=methoxymethyl group, and R²=methyl group) (the total yield through the three steps: 62%).

$^1$H-NMR (400 MHz, CDCl$_3$) δ1.98-2.15 (2H, m), 3.01 (3H, s), 3.40 (3H, s), 3.59-3.68 (2H, m), 3.92 (1H, m), 4.36 (1H, m), 4.71 (2H, dd, J=8.0, 13.6 Hz).

[Example 4-2] Production of (3S)-4-chloro-3-(1-ethoxyethyloxy)-butyl methanesulfonate Ester (a Compound of the Formula (4), Wherein X=Cl, P=Ethoxyethyl Group, and R²=Methyl Group)

In a 1-L reactor, 5.02 g (30.13 mmol) of ethyl (3S)-4-chloro-3-hydroxybutanoate ester (a compound of the formula (1), wherein X=Cl, and R¹=ethyl group), 2.39 g (33.14 mmol) of ethyl vinyl ether, 0.08 g (0.30 mmol) of pyridinium p-toluenesulfonate and 25 mL of toluene were placed and the mixture was stirred for 3 hours at 40° C. to obtain a solution of ethyl (3S)-4-chloro-3-(1-ethoxyethyloxy)-butanoate ester (a compound of the formula (2), wherein X=Cl, P=ethoxyethyl group, and R¹=ethyl group) in toluene.

¹H-NMR (400 MHz, CDCl₃) δ1.18-1.36 (9H, 2.58-2.77 (2H, m), 3.23-3.75 (4H, m), 4.10-4.35 (3H, m), 4.82 (1H, m).

Then, 70 mL (252.25 mmol) of a 70% solution of sodium bis(methoxyethoxy)aluminium hydride in toluene was added to this reaction liquid at 5° C. to 10° C. and the mixture was stirred for 1 hour at 5° C. to 10° C. To this reaction liquid, 3.25 mL of water, 9.53 g of magnesium sulfate, and 3.25 mL of water were added sequentially at 5° C. to 10° C., and the mixture was stirred for 4 hours at 5° C. to 10° C. and filtered to remove solids. Then, the filtrate was washed with saturated brine, dried, and subsequently concentrated to obtain 5.81 g (pure content: 5.44 g) of (3S)-4-chloro-3-(1-ethoxyethyloxy)-butan-1-ol (a compound of the formula (3), wherein X=Cl, and P=ethoxyethyl group) in toluene solution (the total yield through the two steps: 92%).

¹H-NMR (400 MHz, CDCl₃) δ1.17-1.29 (3H, m), 1.30-1.37 (3H, m), 1.61-1.72 (0.6H, m), 1.80-2.00 (2H, m), 3.02 (0.4H, m), 3.50-3.90 (6H, m), 3.92-4.08 (1H, m), 4.79-4.86 (1H, m).

Next, to 4.44 g of this solution (containing 4.16 g (21.17 mmol) of (3S)-4-chloro-3-(l-ethoxyethyloxy)-butan-1-ol (a compound of the formula (3), wherein X=Cl, and P=ethoxyethyl group)), 20 mL of toluene and 2.35 g (23.29 mmol) of triethylamine were added and then 2.55 g (22.23 mmol) of methanesulfonyl chloride was added thereto at 5° C. to 15° C. and the mixture was stirred for 0.5 hour at 5° C. to 10° C. This reaction liquid was washed with water, dried, and then concentrated to obtain 10.83 g (pure content: 5.33 g) of crude (3S)-4-chloro-3-(1-ethoxyethyloxy)-butyl methanesulfonate ester (a compound of the formula (4), wherein X=Cl, P=ethoxyethyl group, and R²=methyl group) in toluene solution (yield: 92%).

¹H-NMR (400 MHz, CDCl₃) δ1.20 (3H, t, J=5.9 Hz), 1.32 (3H, d, J=7.4 Hz), 1.92-2.19 (2H, m), 2.99 (3H, s), 3.43-3.71 (4H, m), 3.88 (0.5H, m), 4.02 (0.5H, m), 4.26-4.40 (2H, m), 4.78 (1H, m).

[Example 4-3] Production of (3S)-4-chloro-3-tert-butyldimethylsilyloxy-butyl methanesulfonate Ester (a Compound of the Formula (4), Wherein X=Cl, P=Tert-Butyldimethylsilyl Group, and R²=Methyl Group)

In a 50-mL reactor, 5.00 g (30.01 mmol) of ethyl (3S)-4-chloro-3-hydroxybutanoate ester (a compound of the formula (1), wherein X=Cl, and R¹=ethyl group), 3.06 g (45.02 mmol) of imidazole and 25 mL of dichloromethane were placed and 5.88 g (39.01 mmol) of tert-butyldimethylsilyl chloride and 1.18 g (11.71 mmol) of methoxymethyl chloride were added thereto on ice and the mixture was stirred at room temperature. After the completion of the reaction, the reaction liquid was washed with water and with saturated aqueous sodium bicarbonate solution, dried, and the concentrated to obtain 8.01 g of crude ethyl (3S)-4-chloro-3-tert-butyldimethylsilyloxy-butanoate ester (a compound of the formula (2), wherein X=Cl, P=tert-butyldimethylsilyl group, and R¹=ethyl group) (yield: 95%).

¹H-NMR (400 MHz, CDCl₃) δ0.05 (3H, s), 0.11 (3H, s), 0.88 (9H, s), 1.26 (3H, t, J=7.4 Hz), 2.49-2.73 (2H, m), 3.52 (2H, s), 4.12 (2H, m), 4.31 (1H, m).

Next, 8.01 g of this crude ethyl (3S)-4-chloro-3-tert-butyldimethylsilyloxy-butanoate ester (a compound of the formula (2), wherein X=Cl, P=tert-butyldimethylsilyl group, and R¹=ethyl group) was dissolved in 25 mL of toluene, and 9.5 mL (34.24 mmol) of a 70% solution of sodium bis(methoxyethoxy)aluminium hydride in toluene was added thereto at 5° C. to 15° C. and the mixture was stirred for 2.5 hours at 5° C. to 10° C. To this reaction liquid, 2.05 mL of acetic acid and 5.55 mL of water were added sequentially at 5° C. to 10° C., and the mixture was stirred for 0.5 hour at room temperature and filtered to remove solids. Then, the filtrate was washed with saturated brine, dried, and subsequently concentrated to obtain 4.66 g (pure content: 4.28 g) of (3S)-4-chloro-3-tert-butyldimethylsilyloxy-butan-1-ol (a compound of the formula (3), wherein X=Cl, and P=tert-butyldimethylsilyl group) in toluene solution (yield: 63%).

¹H-NMR (400 MHz, CDCl₃) δ0.14 (6H, s), 0.92 (9H, s), 1.80-2.01 (3H, m), 3.52 (2H, m), 3.81 (2H, m), 4.10 (1H, m).

Next, 23 mL of toluene and 2.17 mL (21.46 mmol) of triethylamine were added to this solution and then 2.35 g (20.49 mmol) of methanesulfonyl chloride was added thereto at 5° C. to 10° C. and the mixture was stirred for 1 hour at 5° C. to 10° C. This reaction liquid was washed with water, dried, and then concentrated to obtain 6.09 g (pure content: 5.46 g) of (3S)-4-chloro-3-tert-butyldimethylsilyloxy-butyl methanesulfonate ester (a compound of the formula (4), wherein X=Cl, P=tert-butyldimethylsilyl group, and R²=methyl group) in toluene solution (yield: 96%).

¹H-NMR (400 MHz, CDCl₃) δ0.10 (6H, s), 0.89 (9H, s), 1.90-1.99 (1H, m), 2.06-2.17 (1H, m), 3.02 (3H, s), 3.47 (2H, m), 4.03 (1H, m), 4.28-4.40 (2H, m).

[Example 4-4] Production of (3S)-4-chloro-3-tert-butyloxy-butyl methanesulfonate Ester (a Compound of the Formula (4), Wherein X=Cl, P=Tert-Butyl Group, and R²=Methyl Group)

In a 100-mL reactor, 7.51 g (45.11 mmol) of ethyl (3S)-4-chloro-3-hydroxybutanoate ester (a compound of the formula (1), wherein X=Cl, and R¹=ethyl group) and 18 mL of n-hexane were placed and 0.47 g (4.51 mmol) of concentrated sulfuric acid and 6.17 g (110.07 mmol) of isobutylene were added thereto on ice and the mixture was stirred for 18 hours at 30-35° C. Then, the reaction liquid was washed with saturated aqueous sodium bicarbonate solution, dried, then concentrated, and purified by silica gel chromatography to obtain 4.92 g of ethyl (3S)-4-chloro-3-tert-butyloxy-butanoate ester (a compound of the formula (2), wherein X=Cl, P=tert-butyl group, and R¹=ethyl group) (yield: 49%).

¹H-NMR (400 MHz, CDCl₃) δ1.20 (9H, s), 1.28 (3H, t, J=8 Hz), 2.51-2.76 (2H, m), 3.48-3.60 (2H, m), 4.15 (3H, m).

Next, 4.92 g (22.11 mmol) of this crude ethyl (3S)-4-chloro-3-tert-butyloxy-butanoate ester (a compound of the formula (2), wherein X=Cl, P=tert-butyl group, and R¹=ethyl group) was dissolved in 25 mL of toluene, and 8 mL (28.74 mmol) of a 70% solution of sodium bis(methoxyethoxy)aluminium hydride in toluene was added thereto at 5° C. to 15° C. and the mixture was stirred for 2 hours at 5° C. to 10° C. To this reaction liquid, 0.77 mL of ethanol, 3.41 g of citric acid, and 20 mL of water were added sequentially at 5° C. to 10° C., and the mixture was stirred for 0.5 hour at 5° C. to 10° C., and the separated organic phase was washed with saturated brine, dried, then concentrated, and then purified by silica gel chromatography to obtain 3.29 g of (3S)-4-chloro-3-tert-butyloxy-butan-1-ol (a compound of the formula (3), wherein X=Cl and P=tert-butyl group) (yield: 82%).

¹H-NMR (400 MHz, CDCl₃) δ1.25 (9H, s), 1.80-1.88 (1H, m), 1.94-2.03 (1H, m), 2.58 (1H, brm), 3.44-3.56 (2H, m), 3.75 (1H, m), 3.83 (1H, m), 3.96 (1H, m).

Next, to 2.25 g (12.47 mmol) of the obtained (3S)-4-chloro-3-tert-butyloxy-butan-1-ol (a compound of the formula (3), wherein X=Cl and P=tert-butyl group), 23 mL of toluene and 2.24 mL (16.21 mmol) of triethylamine were added and 1.01 mL (13.09 mmol) of methanesulfonyl chloride was added thereto at 5° C. to 10° C. and the mixture was stirred for 2 hours at 5° C. to 10° C. This reaction liquid was washed with water, dried, and then concentrated to obtain 4.23 g (pure content: 3.19 g) of (3S)-4-chloro-3-tert-butyloxy-butyl methanesulfonate ester (a compound of the formula (4), wherein X=Cl, P=tert-butyl group, and R²=methyl group) in toluene solution (yield: 99%).

¹H-NMR (400 MHz, CDCl₃) δ1.23 (9H, s), 1.88-1.96 (1H, m), 2.12-2.21 (1H, m), 3.02 (3H, s), 3.39-3.57 (2H, m), 3.86 (1H, m), 4.35 (2H, m).

[Example 4-5] Production of (3S)-4-chloro-3-methoxymethyloxy-butyl p-toluenesulfonate Ester (a Compound of the Formula (4), Wherein X=Cl, P=Methoxymethyl Group, and R²=p-Tolyl Group)

To 2.22 g (pure content: 2.00 g, 11.86 mmol) of the (3S)-4-chloro-3-methoxymethyloxy-butan-1-ol (a compound of the formula (3), wherein X=Cl, P=methoxymethyl group) obtained in accordance with Example 4, 9 mL of toluene and 1.00 g (13.10 mmol) of pyridine were added, and 2.40 g (12.50 mmol) of p-toluenesulfonyl chloride and 29 mg (0.24 mmol) of 4-dimethylaminopyridine were added thereto at room temperature and the mixture was stirred for 16 hours at 40° C. This reaction liquid was washed with water, dried, then concentrated, and purified by silica gel chromatography to obtain 1.75 g of (3S)-4-chloro-3-methoxymethyloxy-butyl p-toluenesulfonate ester (a compound of the formula (4), wherein X=Cl, P=methoxymethyl group, and R²=p-tolyl group) (yield: 46%).

¹H-NMR (400 MHz, CDCl₃) δ1.88-2.03 (2H, m), 2.46 (3H, s), 3.35 (3H, s), 3.53-3.66 (2H, m), 3.87 (1H, m), 4.09-4.20 (4H, m), 4.61 (2H, m), 7.35 (2H, d, J=8.4 Hz), 7.79 (2H, d, J=8.4 Hz).

[Example 4-6] Production of (3S)-4-chloro-3-(1-ethoxyethyloxy)-butyl p-toluenesulfonate Ester (a Compound of the Formula (4), Wherein X=Cl, P=Ethoxyethyl Group, and R²=p-Tolyl Group)

To 1.31 g (pure content: 6.23 mmol) of the (3S)-4-chloro-3-(1-ethoxyethyloxy)-butan-1-ol (a compound of the formula (3), wherein X=Cl, and P=ethoxyethyl group) obtained in accordance with Example 4-2, 6.1 mL of toluene, 0.69 g (6.85 mmol) of triethylamine, 1.19 g (6.23 mmol) of p-toluenesulfonyl chloride and 0.76 g (6.23 mmol) of 4-dimethylaminopyridine were added and the mixture was stirred for 33 hours at 40° C. This reaction liquid was washed with water, dried, then concentrated, and purified by silica gel chromatography to obtain 0.95 g (pure content: 0.44 g) of (3S)-4-chloro-3-(1-ethoxyethyloxy)-butyl p-toluenesulfonate ester (a compound of the formula (4), wherein X=Cl, P=ethoxyethyl group, and R²=p-tolyl group) (yield: 20%).

¹H-NMR (400 MHz, CDCl₃) δ1.12-1.38 (6H, m), 1.80-2.10 (2H, m), 2.43 (3H, s), 3.40-3.85 (4H, m), 3.93-4.23 (3H, m), 4.80 (1H, m), 7.36 (2H, m), 7.80 (2H, m). one-(tetrahydropyran-2-yloxy)-butyl]malonate Ester (a Compound of the Formula (6), Wherein X=Cl, P=Tetrahydropyranyl Group, R³=Ethyl Group, and A=Methyl Group)

In a 20-mL reactor, 0.10 g (0.46 mmol) of diethyl acetaminomalonate ester (a compound of the formula (5), wherein R³=ethyl group and A=methyl group) and 1 mL of toluene were placed, and 180 μL (0.46 mmol) of 20% sodium ethoxide was added thereto and the mixture was stirred for 1.5 hours at 25° C. To this mixture, 0.5 mL of the toluene solution containing 0.15 g (pure content: 0.13 g, 0.46 mmol) of the crude (3S)-4-chloro-3-(tetrahydropyran-2-yloxy)-butyl methanesulfonate ester (a compound of the formula (4), wherein X=Cl, P=tetrahydropyranyl group, and R²=methyl group) obtained in Example 2, 0.08 g (0.46 mmol) of potassium iodide, and 1 mL of ethanol were added at 25° C. and heated to reflux overnight. Ethyl acetate was added to this reaction liquid and the resulting reaction liquid was washed with water, dried, then concentrated, and purified by silica gel column chromatography to obtain 0.12 g of diethyl (3S)-2-acetylamino-2-[4-chloro-3-(tetrahydropyran-2-yloxy)-butyl]malonate ester (a compound of the formula (6), wherein X=Cl, P=tetrahydropyranyl group, R³=ethyl group, and A=methyl group) (yield: 63%).

[Example 6] Production of diethyl (3S)-2-acetylamino-2-[4-chloro-3-(tetrahydropyran-2-yloxy)-butyl]malonate Ester (a Compound of the Formula (6), Wherein X=Cl, P=Tetrahydropyranyl Group, R³=Ethyl Group, and A=Methyl Group)

In a 50-mL reactor, 0.68 g (3.15 mmol) of diethyl acetaminomalonate ester (a compound of the formula (5), wherein R³=ethyl group and A=methyl group) and 3.4 mL of N,N-dimethylformamide were placed, and 0.29 g (3.00 mmol) of sodium tert-butoxide was added thereto and the mixture was stirred for 1 hour at 30° C. To this mixture, 4 mL of the toluene solution containing 1.01 g (pure content: 0.86 g, 3.00 mmol) of the crude (3S)-4-chloro-3-(tetrahydropyran-2-yloxy)-butyl methanesulfonate ester (a compound of the formula (4), wherein X=Cl, P=tetrahydropyranyl group, and R²=methyl group) obtained in Example 3 and 0.10 g (0.6 mmol) of potassium iodide were added at 30° C. and the mixture was stirred for 7.5 hours at 60° C. This reaction liquid was washed with water, dried, and then concentrated to obtain 1.22 g (pure content: 1.01 g) of crude diethyl (3S)-2-acetylamino-2-[4-chloro-3-(tetrahydropyran-2-yloxy)-butyl]malonate ester (a compound of the formula (6), wherein X=Cl, P=tetrahydropyranyl group, R³=ethyl group, and A=methyl group) (yield: 83%).

¹H-NMR (400 MHz, CDCl₃) δ1.25 (6H, m), 1.15-1.83 (8H, m), 2.03 (3H, s), 2.30-2.50 (2H, m), 3.47-3.95 (5H, m), 4.20-4.30 (4H, m), 4.61 and 4.72 (1H, m), 6.80 (1H, brs).

[Example 7-1] Production of diethyl (3S)-2-acetylamino-2-(4-chloro-3-methoxymethyloxy-butyl)malonate Ester (a Compound of the Formula (6), Wherein X=Cl, P=Methoxymethyl Group, R³=Ethyl Group, and A=Methyl Group)

In a 30-mL reactor, 0.49 g (2.27 mmol) of diethyl acetaminomalonate ester (a compound of the formula (5), wherein R³=ethyl group and A=methyl group) and 2.5 mL of dimethylsulfoxide were placed, and 0.23 g (2.38 mmol) of sodium tert-butoxide was added thereto and the mixture was stirred for 2 hours at 30° C. To this mixture, 2.5 mL of the toluene solution containing 0.56 g (2.27 mmol) of the crude (3S)-4-chloro-3-methoxymethyloxy-butyl methanesulfonate ester (a compound of the formula (4), wherein X=Cl, P=methoxymethyl group, and $R^2$=methyl group) obtained in Example 4 and 0.08 g (0.45 mmol) of potassium iodide were added at 30° C. and the mixture was stirred for 5 hours at 80° C. An aliquot of 200 µL was withdrawn from this reaction liquid and ethyl acetate was added thereto and the resulting mixture was washed with water, dried, and then concentrated to obtain 25 mg of diethyl (3S)-2-acetylamino-2-(4-chloro-3-methoxymethyloxy-butyl)malonate ester (a compound of the formula (6), wherein X=Cl, P=methoxymethyl group, $R^3$=ethyl group, and A=methyl group) (yield: 94%).

$^1$H-NMR (400 MHz, CDCl$_3$) δ1.23 (6H, t, J=5.2 Hz), 1.33-1.50 (2H, m), 2.01 (3H, s), 2.30-2.46 (2H, m), 3.36 (3H, s), 3.55 (2H, d, J=5.2 Hz), 3.67 (1H, m), 4.21 (4H, q, J=7.3 Hz), 4.64 (2H, dd, J=7.2, 18 Hz), 6.77 (1H, brs).

[Example 7-2] Production of diethyl (3S)-2-acetylamino-2-(4-chloro-3-(1-ethoxyethyloxy)-butyl)malonate Ester (a Compound of the Formula (6), Wherein X=Cl, P=Ethoxyethyl Group, $R^3$=Ethyl Group, and A=Methyl Group)

In a 50-mL reactor, 4.95 g (22.82 mmol) of diethyl acetaminomalonate ester (a compound of the formula (5), wherein $R^3$=ethyl group and A=methyl group) and 22 mL of N,N-dimethylformamide were placed, and 2.15 g (22.40 mmol) of sodium tert-butoxide was added thereto and the mixture was stirred for 1.5 hours at 40° C. To this mixture, 10.83 g (pure content: 5.33 g, 19.41 mmol) of the toluene solution containing the crude (3S)-4-chloro-3-(1-ethoxyethyloxy)-butyl methanesulfonate ester (a compound of the formula (4), wherein X=Cl, P ethoxyethyl group, and $R^2$=methyl group) obtained in Example 4-2, 4 mL of toluene and 0.69 g (4.16 mmol) of potassium iodide were added at 40° C. and the mixture was stirred for 2 hours at 80° C. Toluene was added to this reaction liquid and the resulting reaction liquid was washed with water, dried, and then concentrated to obtain 7.64 g (pure content: 7.14 g; yield: 93%) of diethyl (3S)-2-acetylamino-2-(4-chloro-3-(1-ethoxyethyloxy)-butyl)malonate ester (a compound of the formula (6), wherein X=Cl, P=ethoxyethyl group, $R^3$=ethyl group, and A=methyl group).

$^1$H-NMR (400 MHz, CDCl$_3$) δ1.15-1.32 (12H, m), 1.30-1.60 (2H, m), 2.03 (3H, s), 2.30-2.52 (2H, m), 3.47-3.83 (5H, m), 4.23 (4H, q, J=7.0 Hz), 4.73 and 4.81 (1H, m), 6.78 (1H, brs).

[Example 7-3] Production of diethyl (3S)-2-acetylamino-2-(4-chloro-3-tert-butyldimethylsilyloxy-butyl)malonate Ester (a Compound of the Formula (6), Wherein X=Cl, P=Tert-Butyldimethylsilyl Group, $R^3$=Ethyl Group, and A=Methyl Group)

In a 50-mL reactor, 1.15 g (5.29 mmol) of diethyl acetaminomalonate ester (a compound of the formula (5), wherein $R^3$=ethyl group and A=methyl group) and 6.8 mL of N,N-dimethylformamide were placed, and 0.50 g (5.19 mmol) of sodium tert-butoxide was added thereto and the mixture was stirred for 1 hour at 40° C. To this mixture, 1.70 g (pure content: 1.52 g, 4.81 mmol) of the toluene solution containing the crude (3S)-4-chloro-3-tert-butyldimethylsilyloxy-butyl methanesulfonate ester (a compound of the formula (4), wherein X=Cl, P=tert-butyldimethylsilyl group, and $R^2$=methyl group) obtained in Example 4-3, 1 mL of toluene and 0.16 g (0.96 mmol) of potassium iodide were added at 40° C. and the mixture was stirred for 4 hours at 80° C. Toluene was added to this reaction liquid and the resulting reaction liquid was washed with water, dried, and then concentrated to obtain 2.10 g (pure content: 1.77 g; yield: 84%) of diethyl (3S)-2-acetylamino-2-(4-chloro-3-tert-butyldimethylsilyloxy-butyl)malonate ester (a compound of the formula (6), wherein X=Cl, P=tert-butyldimethylsilyl group, $R^3$=ethyl group, and A=methyl group).

$^1$H-NMR (400 MHz, CDCl$_3$) δ0.09 (6H, s), 0.90 (9H, s), 1.24 (6H, t, J=7.5 Hz), 1.29-1.55 (2H, m), 2.02 (3H, s), 2.30-2.50 (2H, m), 3.42 (2H, m), 3.83 (1H, m), 4.25 (4H, m), 6.75 (1H, brs).

[Example 7-4] Production of diethyl (3S)-2-acetylamino-2-(4-chloro-3-tert-butyloxy-butyl)malonate Ester (a Compound of the Formula (6), Wherein X=Cl, P=Tert-Butyl Group, $R^3$=Ethyl Group, and A=Methyl Group)

In a 50-mL reactor, 0.87 g (4.00 mmol) of diethyl acetaminomalonate ester (a compound of the formula (5), wherein $R^3$=ethyl group and A=methyl group) and 4.3 mL of N,N-dimethylformamide were placed, and 0.38 g (3.92 mmol) of sodium tert-butoxide was added thereto and the mixture was stirred for 1 hour at 40° C. To this mixture, 1.25 g (pure content: 0.94 g, 3.64 mmol) of the toluene solution containing the crude (3S)-4-chloro-3-tert-butyloxy-butyl methanesulfonate ester (a compound of the formula (4), wherein X=Cl, P=tert-butyl group, and $R^2$=methyl group) obtained in Example 4-4, 2 mL of toluene and 0.12 g (0.73 mmol) of potassium iodide were added at 40° C. and the mixture was stirred for 2 hours at 80° C. Toluene was added to this reaction liquid and the resulting reaction liquid was washed with water, dried, then concentrated, and purified by silica gel chromatography to obtain 1.06 g (pure content: 0.95 g; yield: 69%) of diethyl (3S)-2-acetylamino-2-(4-chloro-3-tert-butyloxy-butyl)malonate ester (a compound of the formula (6), wherein X=Cl, P=tert-butyl group, $R^3$=ethyl group, and A=methyl group).

$^1$H-NMR (400 MHz, CDCl$_3$) δ1.19 (9H, s), 1.25 (6H, t, J=7.2 Hz), 1.30-1.38 (1H, m), 1.49-1.59 (1H, m), 2.03 (3H, s), 2.30-2.47 (2H, m), 3.33-3.49 (2H, m), 3.65 (1H, m), 4.27 (4H, q, J=7.2 Hz), 6.78 (1H, brs).

[Example 7-5] Production of diethyl (3S)-2-acetylamino-2-(4-chloro-3-methoxymethyloxy-butyl)malonate Ester (a Compound of the Formula (6), Wherein X=Cl, P=Methoxymethyl Group, $R^3$=Ethyl Group, and A=Methyl Group)

In a 50-mL reactor, 1.04 g (4.81 mmol) of diethyl acetaminomalonate ester (a compound of the formula (5), wherein $R^3$=ethyl group and A=methyl group) and 5.4 mL of N,N-dimethylformamide were placed, and 0.45 g (4.72 mmol) of sodium tert-butoxide was added thereto and the mixture was stirred for 1 hour at 40° C. To this mixture, 5.1 mL of the toluene solution containing 1.80 g (pure content: 1.41 g, 4.37 mmol) of the crude (3S)-4-chloro-3-methoxymethyloxy-butyl p-toluenesulfonate ester (a compound of the formula (4), wherein X=Cl, P=methoxymethyl group, and $R^2$=p-tolyl group) obtained in Example 4-5 and 0.15 g (0.87 mmol) of potassium iodide were added at 40° C. and the mixture was stirred for 2 hours at 80° C. Toluene was added to this reaction liquid and the resulting reaction liquid was washed with water, dried, and then concentrated to obtain 2.08 g (pure content: 1.45 g; yield: 90%) of diethyl (3S)-2-acetylamino-2-(4-chloro-3-methoxymethyloxy-butyl)malonate ester (a compound of the formula (6), wherein X=Cl, P=methoxymethyl group, $R^3$=ethyl group, and A=methyl group).

[Example 8-1] Production of diethyl (3S)-2-benzoylamino-2-[4-chloro-3-(tetrahydropyran-2-yloxy)-butyl]malonate Ester (a Compound of the Formula (6), Wherein X=Cl; P=Tetrahydropyranyl Group, and $R^3$=Ethyl Group, and A=Phenyl Group)

In a 30-mL reactor, 0.38 g (1.37 mmol) of diethyl benzoylaminomalonate ester (a compound of the formula (5), wherein $R^3$=ethyl group and A=phenyl group) and 1.9 mL of N,N-dimethylformamide were placed, and 0.13 g (1.37 mmol) sodium tert-butoxide was added thereto and the mixture was stirred for 1 hour at room temperature. To this mixture, 1.9 mL of the toluene solution containing 0.51 g (pure content: 0.39 g, 1.37 mmol) of the crude (3S)-4-chloro-3-(tetrahydropyran-2-yloxy)-butyl methanesulfonate ester (a compound of the formula (4), wherein X=Cl, P=tetrahydropyranyl group, and $R^2$=methyl group) obtained in Example 3 and 0.09 g (0.55 mmol) of potassium iodide were added at room temperature and the mixture was stirred for 1 hour at 80° C. A small volume of aliquot was withdrawn from this reaction liquid and toluene was added thereto and the resulting mixture was washed with water, dried, and then concentrated to obtain 27 mg of crude diethyl (3S)-2-benzoylamino-2-[4-chloro-3-(tetrahydropyran-2-yloxy)-butyl]malonate ester (a compound of the formula (6), wherein X=Cl, P=tetrahydropyranyl group, and $R^3$=ethyl group, and A=phenyl group).
$^1$H-NMR (400 MHz, CDCl$_3$) δ1.20 (6H, m), 1.32-1.80 (8H, m), 1.97-2.20 (1H, m), 2.40-2.57 (1H, m), 3.16-3.92 (5H, m), 4.20 (4H, m), 4.52 and 4.65 (1H, m), 7.30 (3H, m), 7.80 (2H, m).

[Example 8-2] Production of diethyl (3S)-2-benzoylamino-2-[4-chloro-3-(methoxymethyloxy-butyl]malonate Ester (a Compound of the Formula (6), Wherein X=Cl, P=Methoxymethyl Group, $R^3$=Ethyl Group, and A=Phenyl Group)

In a 50-mL reactor, 1.87 g (6.69 mmol) of diethyl benzoylaminomalonate ester (a compound of the formula (5), wherein $R^3$=ethyl group and A=phenyl group) and 5.7 mL of N,N-dimethylformamide were placed, and 0.63 g (6.57 mmol) of sodium tert-butoxide was added thereto and the mixture was stirred for 1 hour at 40° C. To this mixture, 6 mL of the toluene solution containing 1.50 g (6.08 mmol) of the crude (3S)-4-chloro-3-(tetrahydropyran-2-yloxy)-butyl methanesulfonate ester (a compound of the formula (4), wherein X=Cl, P=methoxymethyl group, and $R^2$=methyl group) obtained in Example 3 and 0.20 g (1.22 mmol) of potassium iodide were added at 40° C. and the mixture was stirred for 2 hours at 80° C. Toluene was added to this reaction liquid and the resulting reaction liquid was washed with water, dried, and then concentrated to obtain 2.83 g (pure content: 2.20 g; yield: 84%) of crude diethyl (3S)-2-benzoylamino-2-[4-chloro-3-methoxymethyloxy-butyl]malonate ester (a compound of the formula (6), wherein X=Cl, P=methoxymethyl group, $R^3$=ethyl group, and A=phenyl group).

$^1$H-NMR (400 MHz, CDCl$_3$) δ1.26 (6H, t, J=7.5 Hz), 1.20-1.85 (8H, m), 2.45-2.65 (2H, m), 3.40-3.92 (5H, m), 4.29 (4H, m), 4.60 and 4.71 (1H, m), 7.42-7.55 (4H, m), 7.82 (2H, m).

[Example 8-3] Production of diethyl (3S)-2-benzoylamino-2-[4-chloro-3-(1-ethoxyethyloxy)-butyl]malonate Ester (a Compound of the Formula (6), Wherein X=Cl, P=Ethoxyethyl Group, $R^3$=Ethyl Group, and A=Phenyl Group)

In a 30-mL reactor, 2.31 g (8.27 mmol) of diethyl benzoylaminomalonate ester (a compound of the formula (5), wherein $R^3$=ethyl group and A=phenyl group) and 8 mL of N,N-dimethylformamide were placed, and 0.78 g (8.12 mmol) of sodium tert-butoxide was added thereto and the mixture was stirred for 2 hours at 40° C. To this mixture, 4 mL of the toluene solution containing 2.06 g (pure content: 1.99 g, 7.52 mmol) of the crude (3S)-4-chloro-3-(1-ethoxyethyloxy)-butyl methanesulfonate ester (a compound of the formula (4), wherein X=Cl, P=ethoxyethyl group, and $R^2$=methyl group) obtained in accordance with Example 4-2 and 0.25 g (1.50 mmol) of potassium iodide were added at 40° C. and the mixture was stirred for 4.5 hours at 80° C. Toluene was added to this reaction liquid and the resulting reaction liquid was washed with water, dried, then concentrated, and purified by silica gel chromatography to obtain 2.31 g of diethyl (3S)-2-benzoylamino-2-[4-chloro-3-(1-ethoxyethyloxy)-butyl]malonate ester (a compound of the formula (6), wherein X=Cl, P=ethoxyethyl group, $R^3$=ethyl group, and A=phenyl group) (yield: 67%).
$^1$H-NMR (400 MHz, CDCl$_3$) δ1.13-1.35 (12H, m), 1.40-1.63 (2H, m), 2.45-2.65 (2H, m), 3.43-3.83 (5H, m), 4.30 (4H, m), 4.72 and 4.80 (1H, m), 7.43-7.58 (4H, m), 7.83 (2H, m).

[Example 8-4] Production of diethyl (3S)-2-benzoylamino-2-[4-chloro-3-tert-butyldimethylsilyloxy-butyl]malonate Ester (a Compound of the Formula (6), Wherein X=Cl, P=Tert-Butyldimethylsilyl Group, $R^3$=Ethyl Group, and A=Phenyl Group)

In a 30-mL reactor, 1.48 g (5.29 mmol) of diethyl benzoylaminomalonate ester (a compound of the formula (5), wherein $R^3$=ethyl group and A=phenyl group) and 6.8 mL of N,N-dimethylformamide were placed, and 0.50 g (5.19 mmol) of sodium tert-butoxide was added thereto and the mixture was stirred for 1 hour at 40° C. To this mixture, 1 mL of the toluene solution containing 1.70 g (pure content: 1.52 g, 4.81 mmol) of the crude (3S)-4-chloro-3-tert-butyldimethylsilyloxy-butyl methanesulfonate ester (a compound of the formula (4), wherein X=Cl, P=tert-butyldimethylsilyl group, and $R^2$=methyl group) obtained in Example 4-3 and 0.16 g (0.96 mmol) of potassium iodide were added at 40° C. and the mixture was stirred for 4.5 hours at 80° C. Toluene was added to this reaction liquid and the resulting reaction liquid was washed with water, dried, and then concentrated to obtain 2.68 g of crude diethyl (3S)-2-benzoylamino-2-[4-chloro-3-tert-butyldimethylsilyloxy-butyl]malonate ester (a compound of the formula (6), wherein X=Cl, P=tert-butyldimethylsilyl group, $R^3$=ethyl group, and A=phenyl group) (pure content: 1.95 g; yield: 81%).
$^1$H-NMR (400 MHz, CDCl$_3$) δ0.10 (6H, s), 0.90 (9H, s), 1.30 (6H, t, J=8.3 Hz), 1.35-1.65 (2H, m), 2.48-2.65 (2H, m), 3.43 (2H, m), 3.85 (1H, m), 4.33 (4H, m), 7.45-7.60 (4H, m), 7.84 (2H, m).

[Example 8-5] Production of diethyl (3S)-2-benzoylamino-2-[4-chloro-3-tert-butyloxy-butyl]malonate Ester (a Compound of the Formula (6), Wherein X=Cl, P=Tert-Butyl Group, $R^3$=Ethyl Group, and A=Phenyl Group)

In a 50-mL reactor, 1.12 g (4.00 mmol) of diethyl benzoylaminomalonate ester (a compound of the formula (5), wherein $R^3$=ethyl group and A=phenyl group) and 4.4 mL of N,N-dimethylformamide were placed, and 0.38 g (3.92 mmol) of sodium tert-butoxide was added thereto and the mixture was stirred for 1 hour at 40° C. To this mixture, 2 mL of the toluene solution containing 1.25 g (pure content: 0.94 g, 3.64 mmol) of the crude (3S)methanesulfonic acid 4-chloro-3-tert-butyloxy-butyl ester (a compound of the formula (4), wherein X=Cl, P=tert-butyl group, and $R^2$=methyl group) obtained in Example 4-4 and 0.12 g (0.73 mmol) of potassium iodide were added at 40° C. and the mixture was stirred for 2 hours at 80° C. Toluene was added to this reaction liquid and the resulting reaction liquid was washed with water, dried, then concentrated, and purified by silica gel chromatography to obtain 1.24 g of diethyl (3S)-2-benzoylamino-2-[4-chloro-3-tert-butyloxy-butyl]malonate ester (a compound of the formula (6), wherein X=Cl, P=tert-butyl group, $R^3$=ethyl group, and A=phenyl group) (pure content: 1.10 g; yield: 69%).

$^1$H-NMR (400 MHz, CDCl$_3$) δ1.16 (9H, s), 1.25-1.29 (7H, m), 1.31-1.42 (1H, m), 2.48-2.57 (2H, m), 3.34-3.49 (2H, m), 3.65 (1H, m), 4.28 (4H, q, J=6.8 Hz), 7.44-7.53 (4H, m), 7.81 (2H, m).

[Example 9] Production of diethyl (5S)-1-acetyl-5-(tetrahydropyran-2-yloxy)-piperidine-2,2-dicarboxylate Ester (a Compound of the Formula (7), Wherein P=Tetrahydropyranyl Group, $R^3$=Ethyl Group, and A=Methyl Group)

In a 100-mL reactor, 5.08 g (pure content: 4.35 g, 10.68 mmol) of the crude diethyl (3S)-2-acetylamino-2-[4-chloro-3-(tetrahydropyran-2-yloxy)-butyl]malonate ester (a compound of the formula (6), wherein X=Cl, P=tetrahydropyranyl group, $R^3$=ethyl group, and A=methyl group) obtained in Example 5, 40 mL of dimethylformamide and 10.44 g (32.04 mmol) of cesium carbonate were placed and the mixture was stirred for 7 hours at 100° C. Toluene was added to this reaction liquid and the resulting reaction liquid was washed with water, dried, and then concentrated to obtain 4.18 g of crude diethyl (5S)-1-acetyl-5-(tetrahydropyran-2-yloxy)-piperidine-2,2-dicarboxylate ester (a compound of the formula (7), wherein P=tetrahydropyranyl group, $R^3$=ethyl group, and A=methyl group) (yield: 94%).

$^1$H-NMR (400 MHz, CDCl$_3$) δ1.15-1.25 (6H, m), 1.32-1.95 (8H, m), 1.95-2.10 (1H, m), 2.10 (3H, s), 2.40-2.50 (1H, m), 3.02 and 3.22 (1H, m), 3.43 (1H, m), 3.55-3.70 (1H, m), 3.72-188 (2H, m), 4.10-4.25 (4H, m), 4.65 (1H, m).

[Example 10] Production of diethyl (5S)-1-acetyl-5-(tetrahydropyran-2-yloxy)-piperidine-2,2-dicarboxylate Ester (a Compound of the Formula (7), Wherein P=Tetrahydropyranyl Group, $R^3$=Ethyl Group, and A=Methyl Group)

In a 100-mL reactor, 5.77 g (pure content: 4.95 g, 12.14 mmol) of the crude diethyl (3S)-2-acetylamino-2-[4-chloro-3-(tetrahydropyran-2-yloxy)-butyl]malonate ester (a compound of the formula (6), wherein X=Cl, P=tetrahydropyranyl group, $R^3$=ethyl group, and A=methyl group) obtained in Example 5 and 58 mL of dimethylformamide were placed and 1.52 g (15.78 mmol) of sodium tert-butoxide were placed therein in three portions over 3 hours at 15° C. and the mixture was stirred for 2 hours at 15° C. An excess amount of the base was neutralized by adding 0.22 mL of acetic acid to this reaction liquid, toluene was added thereto, and the resulting mixture was washed with water, dried, and then concentrated to obtain 3.85 g (pure content: 2.77 g; yield: 62%) of crude diethyl (5S)-1-acetyl-5-(tetrahydropyran-2-yloxy)-piperidine-2,2-dicarboxylate ester (a compound of the formula (7), wherein P=tetrahydropyranyl group, $R^3$=ethyl group, and A=methyl group).

[Example 11-1] Production of diethyl (5S)-1-acetyl-5-(tetrahydropyran-2-yloxy)-piperidine-2,2-dicarboxylate Ester (a Compound of the Formula (7), Wherein P=Tetrahydropyranyl Group, $R^3$=Ethyl Group, and A=Methyl Group)

In a 10-mL reactor, 0.53 g (pure content: 0.5 g, 1.23 mmol) of the crude diethyl (3S)-2-acetylamino-2-[4-chloro-3-(tetrahydropyran-2-yloxy)-butyl]malonate ester (a compound of the formula (6), wherein X=Cl, P=tetrahydropyranyl group, $R^3$=ethyl group, and A=methyl group) obtained in Example 5 and 2.7 mL of dimethylformamide were placed, and potassium carbonate (1.23 mmol) and tetrabutylammonium bromide (hereinafter referred to as "TBAB") (1.227 mmol) were placed therein and the mixture was stirred for 15 hours at 100° C.

Toluene was added to the mixture and the resulting mixture was washed with brine, dried, and then concentrated to obtain 0.61 g (pure content: 0.37 g; yield: 80%) of diethyl (5S)-1-acetyl-5-(tetrahydropyran-2-yloxy)-piperidine-2,2-dicarboxylate ester (a compound of the formula (7), wherein P=tetrahydropyranyl group, $R^3$=ethyl group, and A=methyl group).

[Example 11-2] Production of diethyl (5S)-1-acetyl-5-methoxymethyloxy-piperidine-2,2-dicarboxylate Ester (a Compound of the Formula (7), Wherein P=Methoxymethyl Group, $R^3$=Ethyl Group, and A=Methyl Group)

In a 50-mL reactor, 1.41 g (pure content: 1.12 g, 3.04 mmol) of the crude diethyl (3S)-2-acetylamino-2-[4-chloro-3-methoxymethyloxy-butyl]malonate ester (a compound of the formula (6), wherein X=Cl, P=methoxymethyl group, $R^3$=ethyl group, and A=methyl group) obtained in accordance with Example 7, 5.3 mL of dimethylformamide and 2.97 g (9.12 mmol) of cesium carbonate were placed and the mixture was stirred for 3 hours at 100° C. Toluene was added to this reaction liquid and the resulting reaction liquid was washed with water, dried, and then concentrated to obtain 0.95 g (pure content: 0.87 g; yield: 87%) of crude diethyl (5S)-1-acetyl-5-methoxymethyloxy-piperidine-2,2-dicarboxylate ester (a compound of the formula (7), wherein P=methoxymethyl group, $R^3$=ethyl group, and A=methyl group).

$^1$H-NMR (400 MHz, CDCl$_3$) δ1.27-1.31 (6H, m), 1.50-1.59 (1H, m), 1.80-1.90 (1H, m), 2.08-2.17 (1H, m), 2.17 (3H, s), 2.48-2.55 (1H, m), 3.28-3.40 (1H, m), 3.40 (3H, s), 3.63 (1H, m), 3.76 (1H, m), 4.18-4.30 (4H, m), 4.71 (2H, m).

[Example 11-3] Production of diethyl (5S)-1-acetyl-5-(1-ethoxyethyloxy)-piperidine-2,2-dicarboxylate Ester (a Compound of the Formula (7), Wherein P=Ethoxyethyl Group, $R^3$=Ethyl Group, and A=Methyl Group)

In a 100-mL reactor, 7.64 g (pure content: 7.14 g, 18.06 mmol) of the crude diethyl (3S)-2-acetylamino-2-[4-chloro- 3-(1-ethoxyethyloxy)-butyl]malonate ester (a compound of the formula (6), wherein X=Cl, P=ethoxyethyl group, $R^3$=ethyl group, and A=methyl group) obtained in Example 7-2 and 17.1 mL of dimethylformamide were placed, and 853 mg (21.40 mmol) of 60% sodium hydride was added portion-wise over 5 hours at 40° C. To this reaction liquid, 0.43 mL of acetic acid and toluene were added, and the resulting mixture was washed with water and aqueous 2% potassium carbonate, dried, and then concentrated to obtain 5.64 g (pure content: 5.31 g; yield: 77%) of crude diethyl (5S)-1-acetyl-5-(1-ethoxyethyloxy)-piperidine-2,2-dicarboxylate ester (a compound of the formula (7), wherein P=ethoxyethyl group, $R^3$=ethyl group, and A=methyl group).

$^1$H-NMR (400 MHz, CDCl$_3$) δ1.20-1.35 (12H, m), 1.35-1.50 (1H, m), 1.90 (1H, m), 2.03-2.12 (1H, m), 2.14 (3H, s), 2.47-2.55 (1H, m), 3.02-3.15 and 3.44-3.86 (5H, m), 4.20-4.35 (4H, m), 4.81 (1H, m).

[Example 11-4] Production of diethyl (5S)-1-acetyl-5-tert-butyldimethylsilyloxy-piperidine-2,2-dicarboxylate Ester (a Compound of the Formula (7), Wherein P=Tert-Butyldimethylsilyl Group, $R^3$=Ethyl Group, and A=Methyl Group)

In a 50-mL reactor, 2.10 g (pure content: 1.77 g, 4.05 mmol) of the crude diethyl (3S)-2-acetylamino-2-[4-chloro-3-tert-butyldimethylsilyloxy-butyl]malonate ester (a compound of the formula (6), wherein X=Cl, P=tert-butyldimethylsilyl group, $R^3$=ethyl group, and A=methyl group) obtained in Example 7-3, 8.4 mL of dimethylformamide and 3.96 g (12.15 mmol) of cesium carbonate were placed and the mixture was stirred for 3 hours at 100° C. Toluene was added to this reaction liquid and the resulting reaction liquid was washed with water, dried, then concentrated, and purified by silica gel chromatography to obtain 1.18 g (pure content: 1.13 g; yield: 70%) of diethyl (5S)-1-acetyl-5-tert-butyldimethylsilyloxy-piperidine-2,2-dicarboxylate ester (a compound of the formula (7), wherein P=tert-butyldimethylsilyl group, $R^3$=ethyl group, and A=methyl group).

$^1$H-NMR (400 MHz, CDCl$_3$) δ0.09 (3H, s), 0.10 (3H, s), 0.90 (9H, s), 1.25-1.30 (6H, m), 1.30-1.40 (1H, m), 1.75-1.85 (1H, m), 2.03-2.10 (1H, m), 2.15 (3H, s), 2.49-2.58 (1H, m), 3.02 (1H, dd, J=10.6, 12.1 Hz), 3.58 (1H, dd, J=3.0, 12.1 Hz), 3.83 (1H, m), 4.17-4.31 (4H, m).

[Example 11-5] Production of diethyl (5S)-1-acetyl-5-tert-butyloxy-piperidine-2,2-dicarboxylate Ester (a Compound of the Formula (7), Wherein P=Tert-Butyl Group, $R^3$=Ethyl Group, and A=Methyl Group)

In a 50-mL reactor, 1.06 g (pure content: 0.95 g, 2.50 mmol) of the crude (3S)-2-acetylamino-2-[4-chloro-3-tert-butyloxy-butyl]malonate diethyl ester (a compound of the formula (6), wherein X=Cl, P=tert-butyl group, $R^3$=ethyl group, and A=methyl group) obtained in Example 7-4, 4 mL of dimethylformamide and 2.44 g (7.50 mmol) of cesium carbonate were placed and the mixture was stirred for 4 hours at 100° C. Toluene was added to this reaction liquid and the resulting reaction liquid was washed with water, dried, and then concentrated to obtain 0.73 g (pure content: 0.64 g; yield: 75%) of diethyl (5S)-1-acetyl-5-tert-butyloxy-piperidine-2,2-dicarboxylate ester (a compound of the formula (7), wherein P=tert-butyl group, $R^3$=ethyl group, and A=methyl group).

$^1$H-NMR (400 MHz, CDCl$_3$) δ1.22 (9H, s), 1.25-1.32 (6H, m), 1.35 (1H, m), 1.83-1.87 (1H, m), 2.00-2.07 (1H, m), 2.15 (3H, s), 2.50-2.56 (1H, m), 2.85-2.91 (1H, m), 3.63-3.66 (2H, m); 4.20-4.27 (4H, m).

[Example 11-6] Production of diethyl (5S)-1-benzoyl-5-(tetrahydropyran-2-yloxy)-piperidine-2,2-dicarboxylate Ester (a Compound of the Formula (7), Wherein P=Tetrahydropyranyl Group, $R^3$=Ethyl Group, and A=Phenyl Group)

In a 50-mL reactor, 3.09 g (6.57 mmol) of the crude diethyl (3S)-2-benzoylamino-2-[4-chloro-3-(tetrahydropyran-2-yloxy)-butyl]malonate ester (a compound of the formula (6), wherein X=Cl, P=tetrahydropyranyl group, and $R^3$=ethyl group, and A=phenyl group) obtained in accordance with Example 8, 12 mL of dimethylformamide and 6.42 g (19.71 mmol) of cesium carbonate were placed and the mixture was stirred for 4.5 hours at 100° C. Toluene was added to this reaction liquid and the resulting reaction liquid was washed with water, dried, then concentrated, and purified by silica gel chromatography to obtain 2.08 g (pure content: 1.88 g; yield: 66%) of diethyl (5S)-1-benzoyl-5-(tetrahydropyran-2-yloxy)-piperidine-2,2-dicarboxylate ester (a compound of the formula (7), wherein P tetrahydropyranyl group, $R^3$=ethyl group, and A=phenyl group).

$^1$H-NMR (400 MHz, CDCl$_3$) δ1.23-1.35 (6H, m), 1.43-1.95 (8H, m), 2.20-2.31 (1H, m), 2.57-2.69 (1H, m), 3.22-3.89 (5H, m), 4.22-4.32 (4H, m), 4.50 and 4.69 (1H, m) 7.40 (3H, m), 7.53-7.61 (2H, m).

[Example 11-7] Production of diethyl (5S)-1-benzoyl-5-methoxymethyloxy-piperidine-2,2-dicarboxylate Ester (a Compound of the Formula (7), Wherein P=Methoxymethyl Group, $R^3$=Ethyl Group, and A=Phenyl Group)

In a 50-mL reactor, 1.42 g (pure content: 1.10 g, 2.56 mmol) of the crude diethyl (3S)-2-benzoylamino-2-[4-chloro-3-methoxymethyloxy)-butyl]malonate ester (a compound of the formula (6), wherein X=Cl, P=methoxymethyl group, $R^3$=ethyl group, and A=phenyl group) obtained in accordance with Example 8-2, 5.2 mL of dimethylformamide and 2.50 g (7.68 mmol) of cesium carbonate were placed and the mixture was stirred for 3 hours at 100° C. Toluene was added to this reaction liquid and the resulting reaction liquid was washed with water, dried, and then concentrated to obtain 0.99 g (pure content: 0.93 g; yield: 92%) of diethyl (5S)-1-benzoyl-5-methoxymethyloxy-piperidine-2,2-dicarboxylate ester (a compound of the formula (7), wherein P=methoxymethyl group, $R^3$=ethyl group, and A=phenyl group).

$^1$H-NMR (400 MHz, CDCl$_3$) δ1.29-1.34 (6H, m), 1.58-1.68 (1H, m), 1.81-1.90 (1H, m), 2.21-2.30 (1H, m), 2.55-2.65 (1H, m), 3.20-3.30 (1H, m), 3.28 (3H, s), 3.40 (1H, m), 3.58 (1H, dd, J=3.2, 14.0 Hz), 3.75 (1H, m), 4.20-4.39 (4H, m), 4.54 and 4.63 (1H, d, J=7.2 Hz), 7.42 (3H, m), 7.55 (2H, m).

[Example 11-8] Production of diethyl (5S)-1-benzoyl-5-(1-ethoxyethyloxy)-piperidine-2,2-dicarboxylate Ester (a Compound of the Formula (7), Wherein P=Ethoxyethyl Group, $R^3$=Ethyl Group, and A=Phenyl Group)

In a 50-mL reactor, 2.31 g (5.04 mmol) of the diethyl (3S)-2-benzoylamino-2-[4-chloro-3-(1-ethoxyethyloxy)-butyl]malonate ester (a compound of the formula (6), wherein X=Cl, P=ethoxyethyl group, $R^3$=ethyl group, and A=phenyl group) obtained in Example 8-3, 9.2 mL of dimethylformamide and 4.93 g (15.12 mmol) of cesium carbonate were placed and the mixture was stirred for 5 hours at 100° C. Toluene was added to this reaction liquid and the resulting reaction liquid was washed with water, dried, and then concentrated to obtain 0.92 g of diethyl (5S)-1-benzoyl-5-(1-ethoxyethyloxy)-piperidine-2,2-dicarboxylate ester (a compound of the formula (7), wherein P=ethoxyethyl group, $R^3$=ethyl group, and A=phenyl group) (yield: 43%).

$^1$H-NMR (400 MHz, CDCl$_3$) δ0.99-1.10 (3H, m), 1.17-1.35 (9H, m), 1.45-1.60 (1H, m), 1.83-1.92 (1H, m), 2.18-2.26 (1H, m), 2.57-2.65 (1H, m), 3.11 (1H, m), 4.20-4.33 (4H, m), 4.61 and 4.73 (1H, m), 7.40 (3H, m), 7.52 (2H, m).

[Example 11-9] Production of diethyl (5S)-1-benzoyl-5-tert-butyldimethylsilyloxy-piperidine-2,2-dicarboxylate Ester (a Compound of the Formula (7), Wherein P=Tert-Butyldimethylsilyl Group, $R^3$=Ethyl Group, and A=Phenyl Group)

In a 50-mL reactor, 2.68 g (pure content: 1.95 g, 3.91 mmol) of the diethyl (3S)-2-benzoylamino-2-[4-chloro-3-tert-butyldimethylsilyloxy-butyl]malonate ester (a compound of the formula (6), wherein X=Cl, P=tert-butyldimethylsilyl group, $R^3$=ethyl group, and A=phenyl group) obtained in Example 8-4, 10.7 mL of dimethylformamide, 3.82 g of cesium carbonate (11.73 mmol) were placed and the mixture was stirred for 3 hours at 100° C. Toluene was added to this reaction liquid and the resulting reaction liquid was washed with water, dried, then concentrated, and purified by silica gel chromatography to obtain 1.70 g (pure content: 1.45 g; yield: 80%) of diethyl (5S)-1-benzoyl-5-tert-butyldimethylsilyloxy-piperidine-2,2-dicarboxylate ester (a compound of the formula (7), wherein P=tert-butyldimethylsilyl group, $R^3$=ethyl group, and A=phenyl group).

$^1$H-NMR (400 MHz, CDCl$_3$) δ0.02 (3H, s), 0.03 (3H, s), 0.90 (9H, s), 1.32 (6H, m), 1.50-1.59 (1H, m), 1.77-1.85 (1H, m), 2.20-2.30 (1H, m), 2.62-2.70 (1H, m), 3.16 (1H, dd, J=6.9, 12.0 Hz), 3.50 (1H, dd, J=1.7, 13.7 Hz), 3.83 (1H, m), 4.23-4.37 (4H, m), 4.65 (1H, m), 7.42 (3H, m), 7.58 (2H, m).

[Example 11-10] Production of diethyl (5S)-1-benzoyl-5-tert-butyloxy-piperidine-2,2-dicarboxylate Ester (a Compound of the Formula (7), Wherein P=Tert-Butyl Group, $R^3$=Ethyl Group, and A=Phenyl Group)

In a 50-mL reactor, 1.24 g (pure content: 1.10 g, 2.50 mmol) of the diethyl (3S)-2-benzoylamino-2-[4-chloro-3-tert-butyloxy-butyl]malonate ester (a compound of the formula (6), wherein X=Cl, P=tert-butyl group, $R^3$=ethyl group, and A=phenyl group) obtained in Example 8-5, 5 mL of dimethylformamide and 2.44 g (7.50 mmol) of cesium carbonate were placed and the mixture was stirred for 4 hours at 100° C. Toluene was added to this reaction liquid and the resulting reaction liquid was washed with water, dried, and then concentrated to obtain 1.06 g (pure content: 0.84 g; yield: 83%) of diethyl (5S)-1-benzoyl-5-tert-butyloxy-piperidine-2,2-dicarboxylate ester (a compound of the formula (7), wherein P=tert-butyl group, $R^3$=ethyl group, and A=phenyl group).

$^1$H-NMR (400 MHz, CDCl$_3$) δ1.11 (9H, s), 1.28-1.33 (6H, m), 1.42 (1H, m), 1.80-1.86 (1H, m), 2.17-2.24 (1H, m), 2.60-2.66 (1H, m), 2.94-2.99 (1H, m), 3.56-3.63 (2H, m), 4.26-4.31 (4H, m), 7.38-7.43 (3H, m), 7.54 (2H, m).

D[Example 12-1] Production of diethyl (5S)-1-acetyl-5-hydroxy-piperidine-2,2-dicarboxylate Ester (a Compound of the Formula (8), Wherein $R^3$=Ethyl Group and A=Methyl Group)

In a 100-ml, reactor, 4.18 g (10.68 mmol) of the crude diethyl (5S)-1-acetyl-5-(tetrahydropyran-2-yloxy)-piperidine-2,2-dicarboxylate ester (a compound of the formula (7), wherein P=tetrahydropyranyl group; $R^3$=ethyl group, and A=methyl group) obtained in Example 10, 20 mL of methanol and 19 μL of concentrated hydrochloric acid were placed and the mixture was stirred for 4 hours at room temperature. The reaction was stopped by adding 45 μL of triethylamine to this reaction liquid and methanol was concentrated under vacuum to obtain 3.7 g of an oily substance. Next, this oily substance was dissolved in 20 mL of toluene, 10 mL of n-heptane was added thereto at room temperature for crystallization and another 10 mL of n-heptane was added thereto to allow crystallization to proceed aging at room temperature, and then the crystals were filtered, washed with n-heptane, and dried to obtain 2.30 g of diethyl (5S)-1-acetyl-5-hydroxy-piperidine-2,2-dicarboxylate ester (a compound of the formula (8), wherein $R^3$=ethyl group and A=methyl group) (yield: 75%).

$^1$H-NMR (400 MHz, CDCl$_3$) δ1.20-1.30 (6H, m), 1.40-1.52 (1H, m), 1.80-1.90 (1H, m), 2.09-2.15 (1H, m), 2.15 (3H, s), 2.40-2.50 (1H, m), 3.23 (1H, dd, J=7.6, 14.4 Hz), 3.57 (1H, dd, J=4.8, 12.8 Hz), 3.92 (1H, m), 4.17-4.32 (4H, m).

[Example 12-2] Production of diethyl (5S)-1-acetyl-5-hydroxy-piperidine-2,2-dicarboxylate ester (a compound of the formula (8), wherein $R^3$=ethyl group and A=methyl group)

In a 50-mL reactor, 1.45 g (pure content: 1.28 g, 3.57 mmol) of the crude diethyl (5S)-1-acetyl-5-(1-ethoxyethyloxy)-piperidine-2,2-dicarboxylate ester (a compound of the formula (7), wherein P=ethoxyethyl group, $R^3$=ethyl group, and A=methyl group) obtained in Example 11-3, 7.25 mL of methanol and 10 μL of concentrated hydrochloric acid were placed and the mixture was stirred for 4 hours at room temperature. This reaction liquid was concentrated under vacuum and purified by silica gel chromatography to obtain 0.79 g of diethyl (5S)-1-acetyl-5-hydroxy-piperidine-2,2-dicarboxylate ester (a compound of the formula (8), wherein $R^3$=ethyl group and A=methyl group) (yield: 77%).

[Example 12-3] Production of diethyl (5S)-1-acetyl-5-hydroxy-piperidine-2,2-dicarboxylate Ester (a Compound of the Formula (8), Wherein $R^3$=Ethyl Group and A=Methyl Group)

In a 10-mL reactor, 355 mg (pure content: 342 mg, 0.85 mmol) of the crude (5S)-1-acetyl-5-tert-butyldimethylsilyloxy-piperidine-2,2-dicarboxylate diethyl ester (a compound of the formula (7), wherein P=tert-butyldimethylsilyl group, $R^3$=ethyl group, and A=methyl group) obtained in Example 11-4, 2 mL of methanol and 20 μL of 20% hydrochloric acid were placed and the mixture was stirred for 28.5 hours at room temperature. This reaction liquid was concentrated under vacuum and purified by silica gel chromatography to obtain 171 mg of diethyl (5S)-1-acetyl-5-hydroxy-piperidine-2,2-dicarboxylate ester (a compound of the formula (8), wherein $R^3$=ethyl group and A=methyl group) (yield: 70%).

[Example 12-4] Production of diethyl (5S)-1-acetyl-5-hydroxy-piperidine-2,2-dicarboxylate Ester (a Compound of the Formula (8), Wherein $R^3$=Ethyl Group and A=Methyl Group)

In a 10-mL reactor, 0.30 mg (pure content: 0.26 g, 0.77 mmol) of the crude diethyl (5S)-1-acetyl-5-tert-butyloxy-piperidine-2,2-dicarboxylate ester (a compound of the formula (7), wherein P=tert-butyl group, $R^3$=ethyl group, and A=methyl group) obtained in Example 11-5, 1 mL of toluene and 0.5 mL of trifluoroacetic acid were placed and the mixture was stirred for 48.5 hours at room temperature. To this reaction liquid, 1 mL of triethylamine was added, and the resulting reaction liquid was purified by silica gel chromatography to obtain 0.14 g of diethyl (5S)-1-acetyl-5-hydroxy-piperidine-2,2-dicarboxylate ester (a compound of the formula (8), wherein $R^3$ ethyl group and A=methyl group) (yield: 64%).

[Example 12-5] Production of diethyl (5S)-1-benzoyl-5-hydroxy-piperidine-2,2-dicarboxylate Ester (a Compound of the Formula (8), Wherein $R^3$=Ethyl Group and A=Phenyl Group)

In a 50-mL reactor, 2.08 g (pure content: 1.88 g, 4.33 mmol) of the crude diethyl (5S)-1-benzoyl-5-(tetrahydropyran-2-yloxy)-piperidine-2,2-dicarboxylate ester (a compound of the formula (7), wherein P=tetrahydropyranyl group, $R^3$=ethyl group, and A=phenyl group) obtained in Example 11-6, 10 mL of methanol and 20 µL of concentrated hydrochloric acid were placed and the mixture was stirred for 6 hours at room temperature. The reaction was stopped by adding 100 µL of triethylamine to this reaction liquid, and methanol was concentrated under vacuum, and the resulting mixture was purified by silica gel chromatography to obtain 1.59 g (pure content: 1.46 g; yield: 97%) of diethyl (5S)-1-benzoyl-5-hydroxy-piperidine-2,2-dicarboxylate ester (a compound of the formula (8), wherein $R^3$=ethyl group and A=phenyl group).
$^1$H-NMR (400 MHz, CDCl$_3$) δ1.29-1.35 (6H, m), 1.50-1.65 (1H, m), 1.82-1.90 (1H, m), 2.05 (1H, brs), 2.25-2.33 (1H, m), 2.56-2.62 (1H, m), 3.30 (1H, dd, J=6.8, 13.6 Hz), 3.50 (1H, dd, J=3.2, 14.0 Hz), 3.89 (1H, m), 4.21-4.38 (4H, m), 7.42 (3H, m), 7.52 (2H, m).

[Example 12-6] Production of diethyl (5S)-1-benzoyl-5-hydroxy-piperidine-2,2-dicarboxylate Ester (a Compound of the Formula (8), Wherein $R^3$=Ethyl Group and A=Phenyl Group)

In a 50-mL reactor, 0.38 g (pure content: 0.36 g, 0.92 mmol) of the crude diethyl (5S)-1-benzoyl-5-methoxymethyloxy-piperidine-2,2-dicarboxylate ester (a compound of the formula (7), wherein P=methoxymethyl group, $R^3$=ethyl group, and A=phenyl group) obtained in Example 11-7, 5 mL of methanol and 50 µL of concentrated hydrochloric acid were placed and the mixture was stirred for 4.5 hours at 70° C. This reaction liquid was concentrated under vacuum to obtain 0.30 g (pure content: 0.29 g; yield: 91%) of diethyl (5S)-1-benzoyl-5-hydroxy-piperidine-2,2-dicarboxylate ester (a compound of the formula (8), wherein $R^3$=ethyl group and A=phenyl group).

[Example 12-7] Production of diethyl (5S)-1-benzoyl-5-hydroxy-piperidine-2,2-dicarboxylate Ester (a Compound of the Formula (8), Wherein $R^3$=Ethyl Group and A=Phenyl Group)

In a 50-mL reactor, 0.86 g (2.03 mmol) of the crude diethyl (5S)-1-benzoyl-5-(1-ethoxyethyloxy)-piperidine-2,2-dicarboxylate ester (a compound of the formula (7), wherein P=ethoxyethyl group, $R^3$=ethyl group, and A=phenyl group) obtained in Example 11-8, 4 mL of methanol and 10 µL of concentrated hydrochloric acid were placed and the mixture was stirred for 4 hours at room temperature. The reaction was stopped by adding 100 µL of triethylamine to this reaction liquid, and methanol was concentrated under vacuum, and the resulting mixture was purified by silica gel chromatography to obtain 0.68 g (pure content: 0.60 g; yield: 85%) of diethyl (5S)-1-benzoyl-5-hydroxy-piperidine-2,2-dicarboxylate ester (a compound of the formula (8), wherein $R^3$=ethyl group and A=phenyl group).

[Example 12-8] Production of diethyl (5S)-1-benzoyl-5-hydroxy-piperidine-2,2-dicarboxylate Ester (a Compound of the Formula (8), Wherein $R^3$=Ethyl Group and A=Phenyl Group)

In a 50-mL reactor, 383 mg (pure content: 327 mg, 0.71 mmol) of the crude (5S)1-benzoyl-5-tert-butyldimethylsilyloxy-piperidine-2,2-dicarboxylate diethyl ester (a compound of the formula (7), wherein P=tert-butyldimethylsilyl group, $R^3$=ethyl group, and A=phenyl group) obtained in Example 11-9, 2 mL of methanol and 50 µL of 20% hydrochloric acid were placed and the mixture was stirred for 28.5 hours at room temperature. Then, methanol was concentrated under vacuum and the resulting mixture was purified by silica gel chromatography to obtain 269 mg (pure content: 226 mg; yield: 91%) of diethyl (5S)-1-benzoyl-5-hydroxy-piperidine-2,2-dicarboxylate ester (a compound of the formula (8), wherein $R^3$=ethyl group and A=phenyl group).

[Example 12-9] Production of diethyl (5S)-1-benzoyl-5-hydroxy-piperidine-2,2-dicarboxylate Ester (a Compound of the Formula (8), Wherein $R^3$=Ethyl Group and A Phenyl Group)

In a 50-mL reactor, 0.29 g (pure content: 0.23 g, 0.57 mmol) of the crude diethyl (5S)-1-benzoyl-5-tert-butyloxy-piperidine-2,2-dicarboxylate ester (a compound of the formula (7), wherein P=tert-butyl group, $R^3$=ethyl group, and A=phenyl group) obtained in Example 11-10, 1 mL of toluene and 0.5 mL of trifluoroacetic acid were placed and the mixture was stirred for 48.5 hours at room temperature. Then, ethyl acetate was added thereto and the resulting mixture was washed with saturated aqueous sodium bicarbonate solution, concentrated, and purified by silica gel chromatography to obtain 0.03 g of diethyl (5S)-1-benzoyl-5-hydroxy-piperidine-2,2-dicarboxylate ester (a compound of the formula (8), wherein $R^3$=ethyl group and A=phenyl group) (yield: 15%).

[Example 13] Production of (2S,5S)-5-acetyl-2-oxa-5-azabicyclo[2.2.2]octan-3-one (a Compound of the Formula (9), Wherein A=Methyl Group)

In a 200-mL reactor, 8.7 g (23.45 mmol) of the crude diethyl (5S)-1-acetyl-5-(tetrahydropyran-2-yloxy)-piperidine-2,2-dicarboxylate ester (a compound of the formula (7), wherein P=tetrahydropyranyl group, $R^3$=ethyl group, and A=methyl group) obtained in Example 10, 44 mL of methanol, 43.5 mL of toluene and 0.24 g of 35% hydrochloric acid were placed and the mixture was stirred for 3 hours at room temperature to obtain a solution of diethyl (5S)-1-acetyl-5-hydroxypiperidine-2,2-dicarboxylate ester (a compound of the formula (8), wherein $R^3$=ethyl group and A=methyl group) in methanol and toluene. To this reaction liquid, 3.75 g of sodium hydroxide was added and the mixture was stirred for 3 hours, and methanol was evaporated under vacuum to obtain a toluene solution. Next, 21.1 g of acetic acid and 12.0 g of acetic anhydride were added to this solution and the mixture was stirred for 1 hour at 50° C., 0.47 g of triethylamine was further added thereto, and the mixture was heated to 70° C. and stirred for 5 hours. This reaction liquid was cooled down to 30° C. and 15 mL of toluene was added thereto for deposition and the deposited sodium acetate was removed by filtration, and the filtrate was concentrated to obtain 2.83 g of (2S,5S)-5-acetyl-2-oxa-5-azabicyclo[2.2.2]octan-3-one (a compound of the formula (9), wherein A=methyl group) (yield: 96%).

$^1$H-NMR (400 MHz, CDCl$_3$) δ1.78-2.23 (4H, m), 2.06 and 2.12 (3H, s), 3.55 (1H, t, J=12.4 Hz), 3.65-3.77 (1H, m), 4.38 and 5.19 (1H, m), 4.83-4.90 (1H, m).

[Example 14-1] Production of (2S,5S)-5-acetyl-2-oxa-5-azabicyclo[2.2.2]octan-3-one (a Compound of the Formula (9), Wherein A=Methyl Group)

In a 500-mL reactor, 38.1 g (132.8 mmol) of the diethyl (5S)-1-acetyl-5-hydroxypiperidine-2,2-dicarboxylate ester (a compound of the formula (8), wherein $R^3$=ethyl group and A=methyl group) obtained in Example 12, 190 mL of methanol and 21.2 g of sodium hydroxide were placed and the mixture was stirred for 3 hours at 50° C. to obtain a solution of (5S)-1-acetyl-5-hydroxypiperidine-2,2-dicarboxylic acid disodium salt (compound (8) (a compound with $R^3$=Na and A=methyl group) in methanol. To this reaction liquid, 119.5 g of acetic acid and 1.3 g of triethylamine were added and the mixture was stirred for 1 hour at 95° C. to obtain a mixture of diastereomers of (5S)-1-acetyl-5-hydroxypiperidine-2-carboxylic acid (compounds (11c, 11d)) in a mixed solution of acetic acid and methanol.

(2R,5S)-1-acetyl-5-hydroxypiperidine-2-carboxylic Acid $^1$H-NMR (400 MHz, D$_2$O) δ1.50-1.70 (2H, m), 1.85-2.10 (21-1, m) 2.03 and 2.10 (3H, s), 2.81 (0.3H, d, J=8.9 Hz), 3.35 (0.7H, d, J=8.9 Hz), 3.75 (0.7H, d, J=8.9 Hz), 3.98 (1H, m), 4.26 (0.3H, d, J=8.9 Hz), 4.66 (0.3H, m), 5.08 (0.7H, m)

(2S,5S)-1-acetyl-5-hydroxypiperidine-2-carboxylic Acid $^1$H-NMR (400 MHz, D$_2$O) δ1.23-1.36 (1H, m), 1.59-1.81 (1H, m), 1.98 (1H, m), 2.10 and 2.19 (3H, s), 2.24-2.36 (1H, m), 2.54 (0.4H, t, J=12.6 Hz), 3.03 (0.6H, dd, J=10.7 and 13.3 Hz), 3.55-3.65 (0.6H, m), 3.67-3.76 (0.8H, m), 3.92 (0.6H, dd, J=5.3 and 13.3 Hz), 4.44 (0.6H, m), 4.47 (0.4H, m), 4.94 (0.6H, m)

Next, methanol was evaporated under vacuum from the solution and 108 g of acetic anhydride was added thereto and the mixture was stirred for 3 hours at 100° C. This reaction liquid was cooled down to 30° C. and 190 mL of toluene was added thereto. The deposited sodium acetate was removed by filtration and the filtrate was concentrated to obtain 2.83 g of crude (2S,5S)-5-acetyl-2-oxa-5-azabicyclo[2.2.2]octan-3-one (a compound of the formula (9), wherein A=methyl group) (yield: 72%).

[Example 14-2] Production of (2S,5S)-5-benzoyl-2-oxa-5-azabicyclo[2.2.2]octan-3-one (a Compound of the Formula (9), Wherein A=Phenyl Group)

In a 30-mL reactor, 1.29 g (3.68 mmol) of the diethyl (5S)1-benzoyl-5-hydroxypiperidine-2,2-dicarboxylate ester (a compound of the formula (8), wherein $R^3$=ethyl group and A=phenyl group) obtained in accordance with Example 12-5, 6.5 mL of methanol and 0.29 g (7.36 mmol) of sodium hydroxide were placed and the mixture was heated to reflux for 2 hours and further heated for 14.5 hours after the addition of 0.15 g (3.68 mmol) of sodium hydroxide. Then, the mixture was adjusted on ice to pH 1 with aqueous sulfuric acid solution and the produced inorganic salt was removed by filtration. The mixture was adjusted to pH 2 by addition of sodium acetate and subsequently methanol and water were concentrated to obtain a mixture of diastereomers of (5S)-1-benzoyl-5-hydroxypiperidine-2-carboxylic acid (compounds (11e, 11f)) in a white solid.

(2R,5S)-1-benzoyl-5-hydroxypiperidine-2-carboxylic Acid $^1$H-NMR (400 MHz, D$_2$O) δ1.33-1.85 (2H, m), 2.20 (2H, m), 3.12 (0.5H, d, J=15.0 Hz), 3.40 (0.5H, m), 3.50-3.90 (1H, m), 4.09 (0.5H, brs), 4.47 (0.5H, m), 4.60 (0.5H, d, J=15.0 Hz), 5.46 (0.5H, m), 7.40-7.50 (5H, m).

(2S,5S)-1-benzoyl-5-hydroxypiperidine-2-carboxylic acid $^1$H-NMR (400 MHz, D$_2$O) δ1.33-1.46 (1H, m), 1.65 (0.4H, m), 1.81 (0.6H, m), 2.02 (1H, m), 2.30 (0.4H, m), 2.43 (0.6H, m), 2.72 (0.4H, t, J=12.0 Hz), 3.03 (0.6H, t, J=12.0 Hz), 3.58 (0.6H, m), 3.65 (0.4H, m), 3.80 (0.6H, m), 4.40 (0.4H, m), 4.65 (0.4H, m), 5.40 (0.6H, m), 7.40 (5H, m).

Next, 1.32 mL of acetic acid (22.08 mmol), 5.2 mL of toluene, 0.04 g (0.37 mmol) of triethylamine and 0.57 g (6.38 mmol) of acetic anhydride were added to the white solid and the mixture was stirred for 2.5 hours at 90° C. This reaction liquid was concentrated and toluene was added thereto. The deposited sodium acetate was removed by filtration, and the filtrate was concentrated and purified by silica gel chromatography to obtain 0.76 g (pure content: 0.65 g; yield: 76%) of (2S,5S)-5-benzoyl-2-oxa-5-azabicyclo[2.2.2]octan-3-one (a compound of the formula (9), wherein A=phenyl group).

$^1$H-NMR (400 MHz, CDCl$_3$) δ1.88-2.30 (4H, m), 3.70 (1H, m), 3.90 (1H, m), 4.45 and 4.79 (1H, brs), 4.98 and 5.27 (1H, brs), 7.45 (5H, m).

[Example 15] Production of (2S,5S)-5-hydroxypiperidine-2-carboxylic acid (the Compound (10))

In a 200-mL reactor, 6.36 g (37.59 mmol) of the crude (2S,5S)-5-acetyl-2-oxa-5-azabicyclo[2.2.2]octan-3-one (a compound of the formula (9), wherein A=methyl group) obtained in Example 13 and 93.98 mL (187.97 mmol) of 2 mol/L hydrochloric acid were placed and the mixture was stirred for 3 hours at 90° C. This reaction liquid was concentrated and then dissolved again in water (42.9 mL) and allowed to be adsorbed on strong acidic cation exchange resin (88.69 mL). The resin was washed with water and then elution was performed with ammonia water and the eluted fraction was concentrated to obtain crude (2S,5S)-5-hydroxy-piperidine-2-carboxylic acid (the compound (10)).

The obtained crude (2S,5S)-5-hydroxy-piperidine-2-carboxylic acid (the compound (10)) was dissolved in water (10 mL) and 0.26 g of activated charcoal was added thereto and the mixture was stirred for 2 hours at 40° C. The reaction liquid was filtered and then concentrated, and ethanol was added to the residue to obtain crude crystals, and the obtained crystals were further recrystallized with water/ethanol/acetone to obtain 1.61 g of (2S,5S)-5-hydroxy-piperidine-2-carboxylic acid (the compound (10)) (purity: 96%; yield: 28%).

$^1$H-NMR (400 MHz, CD$_3$OD) δ1.73-1.90 (2H, m), 2.03-2.10 (2H, m), 3.09 (1H, dd, J=2.4, 12.8 Hz), 3.17-3.23 (1H, m), 3.45 (1H, m), 4.02 (1H, m).

[Example 16-1] Production of (2S,5S)-5-hydroxypiperidine-2-carboxylic Acid (the Compound (10))

In a 1000-mL reactor, 18 g of an aqueous acetic acid solution containing 11.31 g (66.90 mmol) of the crude (2S,5S)-5-acetyl-2-oxa-5-azabicyclo[2.2.2]octan-3-one (in the formula (9), A=methyl group) prepared in accordance with Example 13 and 121 mL of 2 mol/L hydrochloric acid were placed and the mixture was stirred for 3 hours at 90° C. To this reaction liquid, 1.2 g of activated charcoal was added and the mixture was stirred for 1 hour at 45° C., and then the activated charcoal was filtered and the filtrate was concentrated to obtain 20.5 g of a residue. Then, this residue was dissolved in 50 mL of water and 175 mL of DIAION® SAT10L (acetate anion type) resin was added thereto and the mixture was stirred for 30 minutes at room temperature and then filtered, and the filtrate was concentrated to obtain 16.5 g of a residue. Then, 2.1 mL of water and 70 mL of ethanol were added to this residue for crystallization at 60° C. and the crystals were filtered at room temperature and dried to obtain 8.0 g of crude crystals of (2S,5S)-5-hydroxy-piperidine-2-carboxylic acid (the compound (10)) (purity: 93%; yield: 77%).

[Example 16-2] Production of (2S,5S)-5-hydroxypiperidine-2-carboxylic Acid Hydrochloride (a Hydrochloride of the Compound (10))

In a 10-mL reactor, 0.43 g (pure content: 0.36 g, 1.58 mmol) of the (2S,5S)-5-benzoyl-2-oxa-5-azabicyclo[2.2.2]octan-3-one (in the formula (9), A=phenyl group) obtained in Example 14-2, 1.5 mL of water and 0.50 g of 35% hydrochloric acid were placed and the mixture was stirred for 15 hours at 100° C. The deposited benzoic acid was removed by filtration and 11.38 g of the obtained filtrate was subjected to the quantification by HPLC. Consequently, it was indicated that the filtrate contained 1.50 mmol of (2S,5S)-5-hydroxypiperidine-2-carboxylic acid hydrochloride (yield: 95%).

The invention claimed is:
1. A compound represented by formula (6a) below:

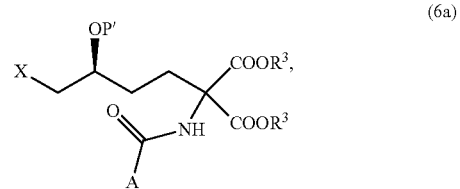

(6a)

wherein X represents Cl, Br, or I, P' represents a tetrahydropyranyl group, methoxymethyl group, ethoxyethyl group, tert-butyl group, or tert-butyldimethylsilyl group, and R$^3$ represents an alkyl group containing 1 to 4 carbon atoms, and A represents an alkyl group containing 1 to 10 carbon atoms, an aryl group containing 6 to 12 carbon atoms, an alkyloxy group containing 1 to 4 carbon atoms, or an aralkyloxy group containing 7 to 20 carbon atoms, or a compound represented by formula (4a) below:

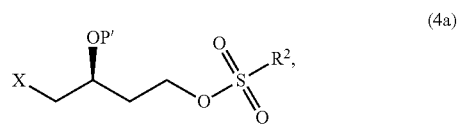

(4a)

wherein X represents Cl, Br, or I, P' represents a tetrahydropyranyl group, methoxymethyl group, ethoxyethyl group, or tert-butyldimethylsilyl group, and R$^2$ represents an alkyl group containing 1 to 10 carbon atoms, an aryl group containing 6 to 12 carbon atoms, or an aralkyl group containing 7 to 20 carbon atoms, or a compound represented by formula (3a) below:

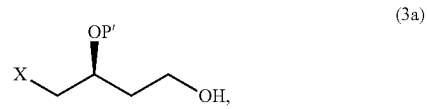

(3a)

wherein X represents Cl, Br, or I, and P' represents a tetrahydropyranyl group, methoxymethyl group, or ethoxyethyl group, or a compound represented by formula (2a) below:

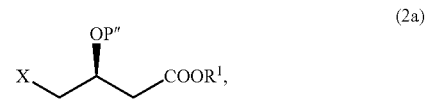

(2a)

wherein X represents Cl, R$^1$ represents a hydrogen atom or an optionally substituted alkyl group containing 1 to 4 carbon atoms, P'' represents a tetrahydropyranyl group or ethoxyethyl group.

2. The compound according to claim 1, wherein the compound represented by the formula (6a) is the compound selected from compounds represented by the formulae below:

(wherein Ac represents an acetyl group and Bz represents a benzoyl group).

3. The compound according to claim 1, wherein the compound represented by the formula (4a) is the compound selected from compounds represented by the formulae below:

(wherein Et represents ethyl group).

4. The compound according to claim 1, wherein the compound represented by the formula (3a) is the compound selected from compounds represented by the formulae below:

(3b)
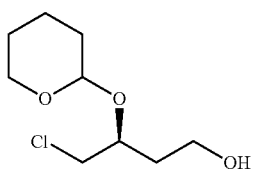

(3c)
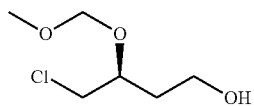

(3d)
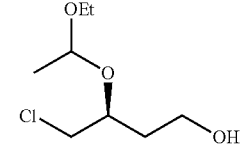

(wherein Et represents ethyl group).

5. The compound according to claim 1, wherein the compound represented by the formula (2a) is the compound selected from compounds represented by the formulae below:

(2b)
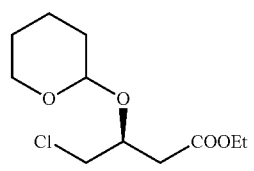

(2d)
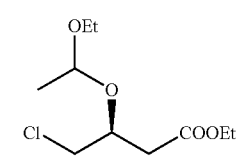

(wherein Et represents ethyl group).

6. The compound (6a) according to claim 1.
7. The compound (4a) according to claim 1.
8. The compound (3a) according to claim 1.
9. The compound (2a) according to claim 1.

10. The compound according to claim 6, wherein the compound represented by the formula (6a) is the compound selected from compounds represented by the formulae below:

(6b)
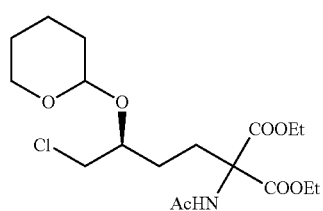

(6c)
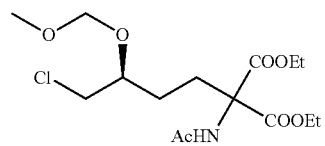

(6d)
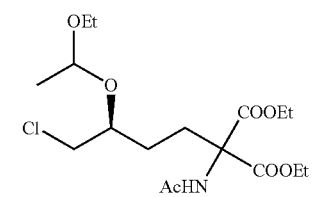

(6e)
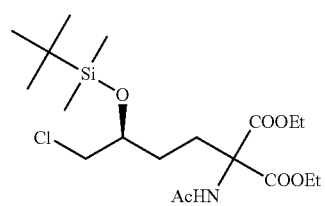

(6f)
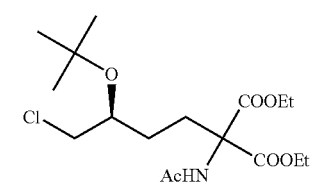

(6g)
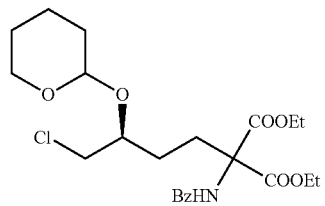

(6h)
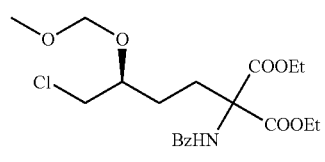

(6i)
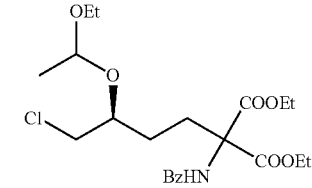

(6j)
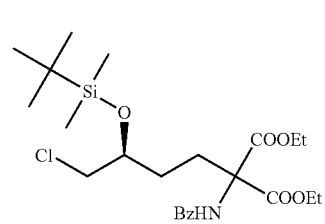

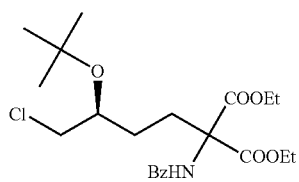

(6k)

(wherein Ac represents an acetyl group and Bz represents a benzoyl group).

11. The compound according to claim 7, wherein the compound represented by the formula (4a) is the compound selected from compounds represented by the formulae below:

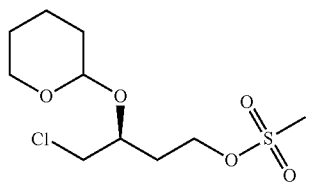

(4b)

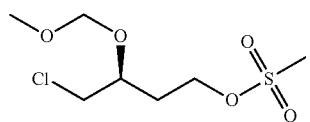

(4c)

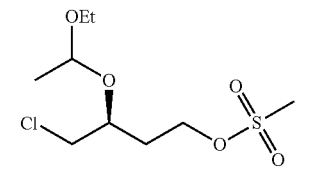

(4d)

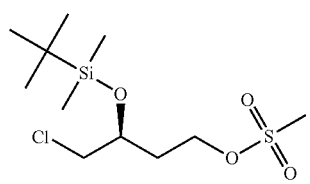

(4e)

(wherein Et represents ethyl group).

12. The compound according to claim 8, wherein the compound represented by the formula (3a) is the compound selected from compounds represented by the formulae below:

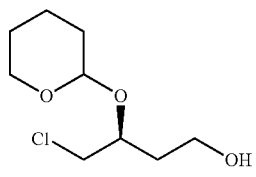

(3b)

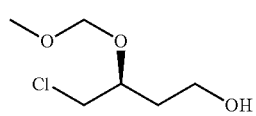

(3c)

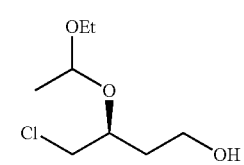

(3d)

(wherein Et represents ethyl group).

13. The compound according to claim 9, wherein the compound represented by the formula (2a) is the compound selected from compounds represented by the formulae below:

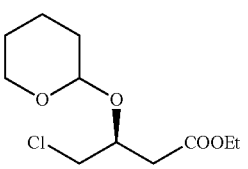

(2b)

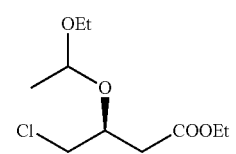

(2d)

(wherein Et represents ethyl group).

* * * * *